United States Patent
Cahill et al.

(10) Patent No.: US 11,660,041 B2
(45) Date of Patent: May 30, 2023

(54) NONINVASIVE THREE-DIMENSIONAL IMAGING OF UTERINE ELECTROPHYSIOLOGY

(71) Applicant: Washington University, St. Louis, MO (US)

(72) Inventors: Alison G. Cahill, St. Louis, MO (US); Phillip S. Cuculich, St. Louis, MO (US); Yong Wang, St. Louis, MO (US); Alan Schwartz, St. Louis, MO (US)

(73) Assignee: Washington University, St. Louis, MO (US)

( * ) Notice: Subject to any disclaimer, the term of this patent is extended or adjusted under 35 U.S.C. 154(b) by 462 days.

(21) Appl. No.: 16/782,693

(22) Filed: Feb. 5, 2020

(65) Prior Publication Data
US 2020/0245923 A1   Aug. 6, 2020

Related U.S. Application Data

(60) Provisional application No. 62/801,422, filed on Feb. 5, 2019.

(51) Int. Cl.
*A61B 5/00* (2006.01)
*A61B 5/055* (2006.01)
*A61B 5/06* (2006.01)

(52) U.S. Cl.
CPC ............ *A61B 5/4356* (2013.01); *A61B 5/004* (2013.01); *A61B 5/0073* (2013.01); *A61B 5/055* (2013.01); *A61B 5/064* (2013.01)

(58) Field of Classification Search
CPC ..... A61B 5/4356; A61B 5/004; A61B 5/0073; A61B 5/055; A61B 5/064; A61B 5/1127; A61B 5/391
See application file for complete search history.

(56) References Cited

U.S. PATENT DOCUMENTS

| | | | |
|---|---|---|---|
| 3,945,373 A | 3/1976 | Tweed et al. | |
| 4,640,295 A | 2/1987 | Isaacson | |
| 5,279,308 A | 1/1994 | DiSabito et al. | |
| 5,984,879 A | 11/1999 | Wallace et al. | |
| 7,016,719 B2 * | 3/2006 | Rudy | A61B 5/6856 600/513 |
| 2003/0199749 A1 | 10/2003 | Lowery, Jr. et al. | |
| 2008/0200822 A1 * | 8/2008 | Schmidt | A61B 6/5247 600/512 |

(Continued)

OTHER PUBLICATIONS

Eswaran, H. et al., "Extraction, quantification and characterization of uterine magnetomyographic activity—A proof of concept case study," Eur. J. Obstet. Gynecol. Reprod. Biol., 2009, pp. S96-S100, vol. 144S.

(Continued)

*Primary Examiner* — Mark D Remaly
(74) *Attorney, Agent, or Firm* — Polsinelli, PC

(57) ABSTRACT

The disclosure provides for a systems and methods for monitoring uterine contractions of a uterus of a mammal by reconstructing three-dimensional images of uterine surface electrical activity based on a noninvasively obtained body-uterus geometry and a plurality of body surface electrical potential maps.

19 Claims, 23 Drawing Sheets
(18 of 23 Drawing Sheet(s) Filed in Color)

(56) References Cited

U.S. PATENT DOCUMENTS

2009/0062683 A1* 3/2009 Calderon ............ A61B 5/4356
600/546

OTHER PUBLICATIONS

Euliano, T. et al., "Monitoring uterine activity during labor: a comparison of 3 methods," Am J. Obstet. Gynecol., Jan. 2013, pp. e1-e6, vol. 208, No. 66.

Harper, L. et al., "The risks and benefits of internal monitors in laboring patients," Am. J. Obstet. Gynecol., Jul. 2013, pp. e1-e6, vol. 209, No. 38.

Hayes-Gill, B. et al., "Accuracy and Reliability of Uterine Contraction Identification Using Abdominal Surface Electrodes," Clin. Med. Insights: Women's Heal., 2012, pp. 65-75, vol. 5.

Jacod, B. et al., "A validation of electrohysterography for uterine activity monitoring during labour," J. Mater. Neonatal Med., 2010, pp. 17-22, vol. 23, No. 1.

Miles, A. et al., "Correlation of External and Internal Monitoring of Uterine Activity in a Cohort of Term Patients," Am. J. Perinatol., 2001, pp. 137-140, vol. 18, No. 3.

\* cited by examiner

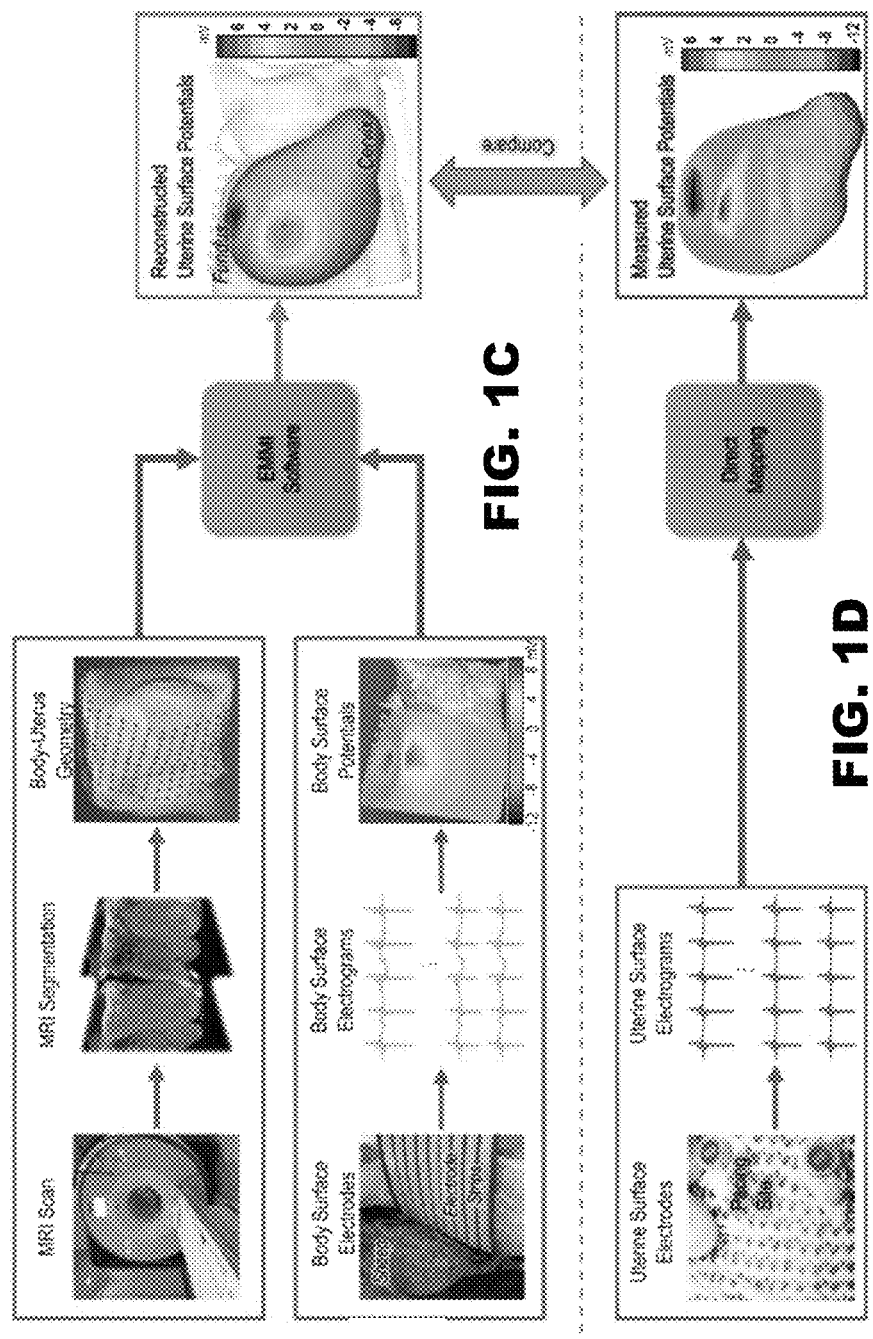

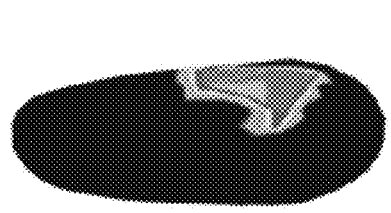
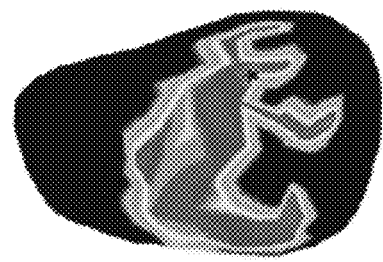
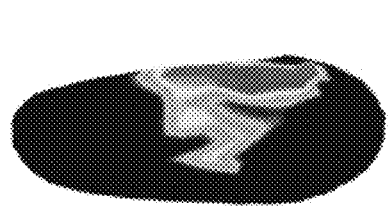
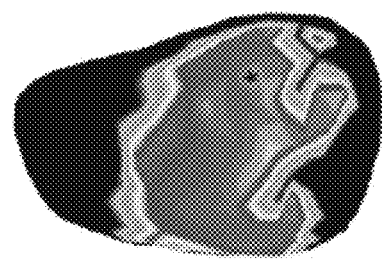
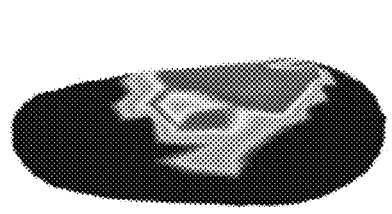
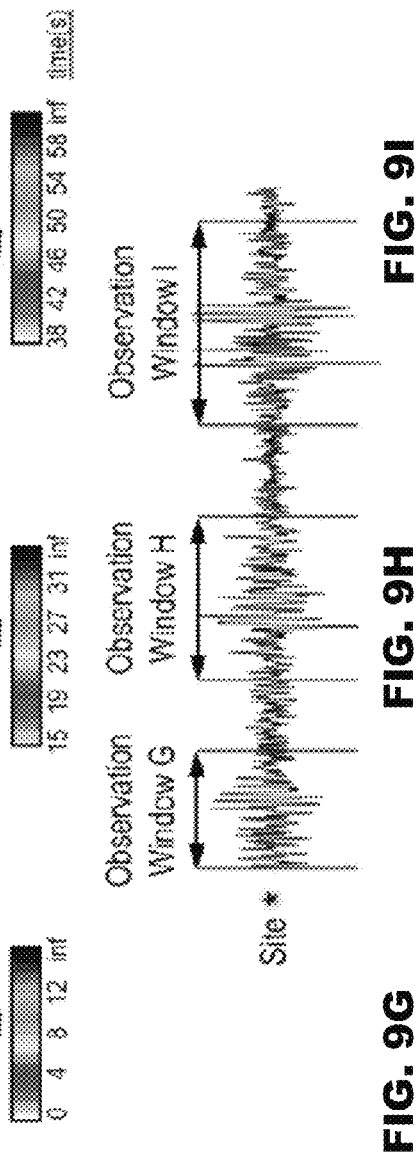
FIG. 9G   FIG. 9H   FIG. 9I

NONINVASIVE THREE-DIMENSIONAL IMAGING OF UTERINE ELECTROPHYSIOLOGY

CROSS REFERENCE TO RELATED APPLICATIONS

This application claims priority to U.S. Provisional Application No. 62/801,422, filed Feb. 5, 2019, the contents of which are entirely incorporated by reference herein.

FIELD

The present disclosure is directed to systems and methods for noninvasively monitoring uterine contractions and more particularly to noninvasively reconstructing three-dimensional images representative of uterine electrical activity during a uterine contraction.

BACKGROUND

Each year, approximately half a million women deliver preterm in the United States, which puts their babies at increased risk of mortality and long-term neurological morbidity. Although 45% of preterm births begin with spontaneous preterm labor, about half of women who go into preterm labor go on to deliver at term. The differences between preterm contractions that cease and those that do not are largely unknown. Moreover, there is a limited understanding of normal term labor, for example, it is still unknown where electrical activity starts during a contraction, how electrical activity propagates to yield localized or global contractions, and whether contractions always start in the same location and propagate in the same manner.

Several techniques have been developed to monitor uterine contractions; however, they present several limitations. Clinicians can manually palpate a patient's abdomen during labor, but this method is time-consuming and observer-dependent. In alternative, intrauterine pressure (IUP) measurement can be performed by transvaginally placing an IUP catheter into the uterus. Although IUP measurement is commonly used and is considered the gold standard for monitoring contractions, this method requires an invasive procedure that poses risks (such as infection) to the mother and potentially to the neonate and thus is only performed when medically necessary. A tocodynamometer (TOCO) transducer can be placed on a patient's abdomen to measure small contour displacements caused by uterine contractions. TOCO transducers are easy to apply and provide information such as contraction frequency and length, but the resulting data only weakly correlate with contraction amplitude data obtained by IUP measurement. Additionally, TOCO requires frequent transducer adjustment and is prone to artifacts caused by other maternal and fetal movements. Magnetomyography (MMG) can be performed by placing an array of sensors in a fix-contoured hemisphere to cover the front of the abdomen during early labor. Although MMG data correlate with contractile events perceived by mothers and provide distribution maps of local uterine activity, this method does not provide a three-dimensional view of the entire uterus and requires a large piece of specialized equipment in a magnetically shielded room. Electrohysterography (EHG) uses a few electrodes placed on the patient's abdomen to measure changes in electrical potential. EHG is promising in that it can detect human uterine contractions and can correlate electrical signal properties with preterm labor. However, EHG is limited to measuring a small area on the maternal abdomen. Finally, uterine electromyography (EMG) can be performed by placing electrodes directly on the uterine surface. EMG has been used in animal studies both in vivo and in vitro, but the invasiveness of the procedure prevents its use in humans. Further, both EHG and EMG lack spatial specificity and thus, cannot accurately measure the exact location of electrical initiation and location-specific propagation patterns of uterine contractions.

It is with these observations in mind, among others, that various aspects of the present disclosure were conceived and developed.

BRIEF SUMMARY

The disclosure provides for a method for noninvasively reconstructing a plurality of generated three-dimensional images to determine uterine electrical activity of a uterus of a mammal during at least one uterine contraction, the mammal having a body surface surrounding the uterus. The method may include applying a plurality of imaging markers to a plurality of locations on the body surface, each one of the plurality of imaging markers applied to one of the plurality of locations; performing an imaging scan of the uterus of the mammal, the imaging scan operable to generate a plurality of generated three-dimensional images of the body surface and uterus of the mammal; determining a body-uterus geometry of the mammal based on the plurality of generated three-dimensional images; replacing each one of the plurality of imaging markers applied to one of a plurality of locations, with one of a plurality of electrodes, each one of the plurality of electrodes in connection with an electrical recording device and operable to detect body surface electrical potentials of the body surface at each one of the plurality of locations; recording the body surface electrical potentials via the electrical recording device during the at least one uterine contraction; generating a plurality of body surface electrical potential maps based on the body-uterus geometry and the plurality of body surface electrical potentials detected at the plurality of locations during the at least one uterine contraction; and/or reconstructing the plurality of generated three-dimensional images to provide a plurality of reconstructed three-dimensional images representative of the uterine electrical activity of the uterus of the mammal during the at least one uterine contraction from the body-uterus geometry of the mammal and the plurality of body surface electrical potentials.

In other aspects, the method may include determining a body-uterus geometry of the uterus of the mammal from a plurality of generated three-dimensional images of a body surface and the uterus of the mammal, the body surface surrounding the uterus of the mammal; detecting a plurality of body surface electrical potentials of the body surface surrounding the uterus of the mammal via a plurality of electrodes, the electrodes in connection with an electrical recording device; recording the plurality of body surface electrical potentials via the electrical recording device during an observation window; and/or determining a uterine surface electrical data by reconstructing the plurality of generated three-dimensional images based on the body-uterus geometry of the mammal and the plurality of body surface electrical potentials.

Further disclosed herein is a system for noninvasively determining uterine surface electrical activity of a mammal during at least one uterine contraction. The system may include a plurality of imaging markers, each one of the plurality of imaging markers operable to be secured to one of a plurality of locations on a body surface surrounding a uterus of a mammal; an imaging modality that is substantially safe for use during pregnancy and is operable to provide a plurality of generated three-dimensional images of the body surface and the uterus of the mammal, the plurality of imaging markers visible on the plurality of generated three-dimensional images; a plurality of electrodes, each one of the plurality of electrodes operable to replace one of the plurality of MRI markers and detect a plurality of electrical signals on the body surface surrounding the uterus of the mammal during the at least one uterine contraction; an electrical mapping device connected to the electrodes and operable to record the plurality of electrical signals detected at each of the plurality of electrodes during the at least one contraction; and/or at least one non-transitory computer readable medium storing instructions which when executed by at least one processor, cause the at least one processor to: receive the plurality of generated three-dimensional images from the imaging modality; determine the plurality of locations based on the imaging markers visible in the plurality of generated three-dimensional images; determine a body-uterus geometry of the mammal based on the plurality of three-dimensional images and the plurality of locations; receive the plurality of electrical signals from the electrical mapping device; and/or generate a plurality of body surface electrical potential maps based on the body-uterus geometry and the plurality of electrical signals.

Additional embodiments and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

BRIEF DESCRIPTION OF THE DRAWINGS

The application file contains at least one drawing executed in color. Copies of this patent application publication with color drawing(s) will be provided by the Office upon request and payment of the necessary fee.

The description will be more fully understood with reference to the following figures and data graphs, which are presented as various embodiments of the disclosure and should not be construed as a complete recitation of the scope of the disclosure, wherein:

FIG. 1C is a flow diagram illustrating additional details of the method of FIG. 1A;

FIG. 1D is a flow diagram of an example method for uterine electromyography used to assess the accuracy of the method of FIG. 1C;

FIG. 9G shows an electrogram and an EMMI-reconstructed activation isochrone map of an oxytocin-induced contraction of the study of FIGS. 7A-7C during observation window G;

FIG. 9H shows an electrogram and an EMMI-reconstructed activation isochrone map of an oxytocin-induced contraction of the study of FIGS. 7A-7C during observation window H;

FIG. 9I shows an electrogram and an EMMI-reconstructed activation isochrone map of an oxytocin-induced contraction of the study of FIGS. 7A-7C during observation window I;

DETAILED DESCRIPTION

Figure 1A:
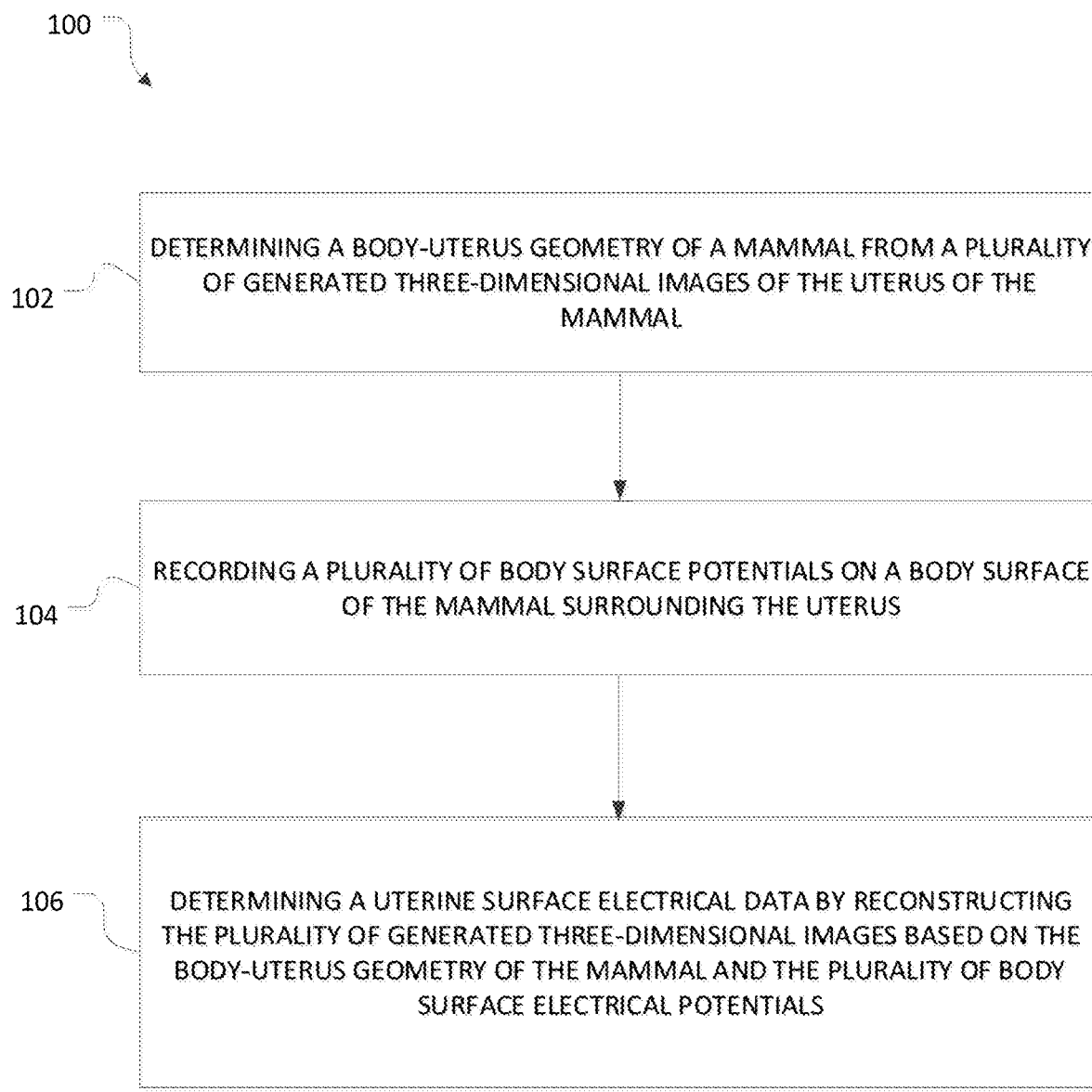
FIG. 1A is a flow diagram of an example method for noninvasive three-dimensional imaging of uterine electrophysiology, also referred to as electromyometrial imaging (EMMI)

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented. The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, condition, or other word that substantially modifies, such that the component or condition need not be exact. The terms "comprising," "including" and "having" are used interchangeably in this disclosure. The terms "comprising," "including" and "having" mean to include, but not necessarily be limited to the things so described.

The methods and systems described herein are constructed to overcome the major disadvantages involved in noninvasively imaging uterine contractions and overcomes some of the issues with the current state of the art for monitoring uterine contractions. The methods and systems herein may have improved safety, accuracy, robustness, and feasibility for evaluation of uterine contractility as compared to the current state of the art.

Figure 1B:
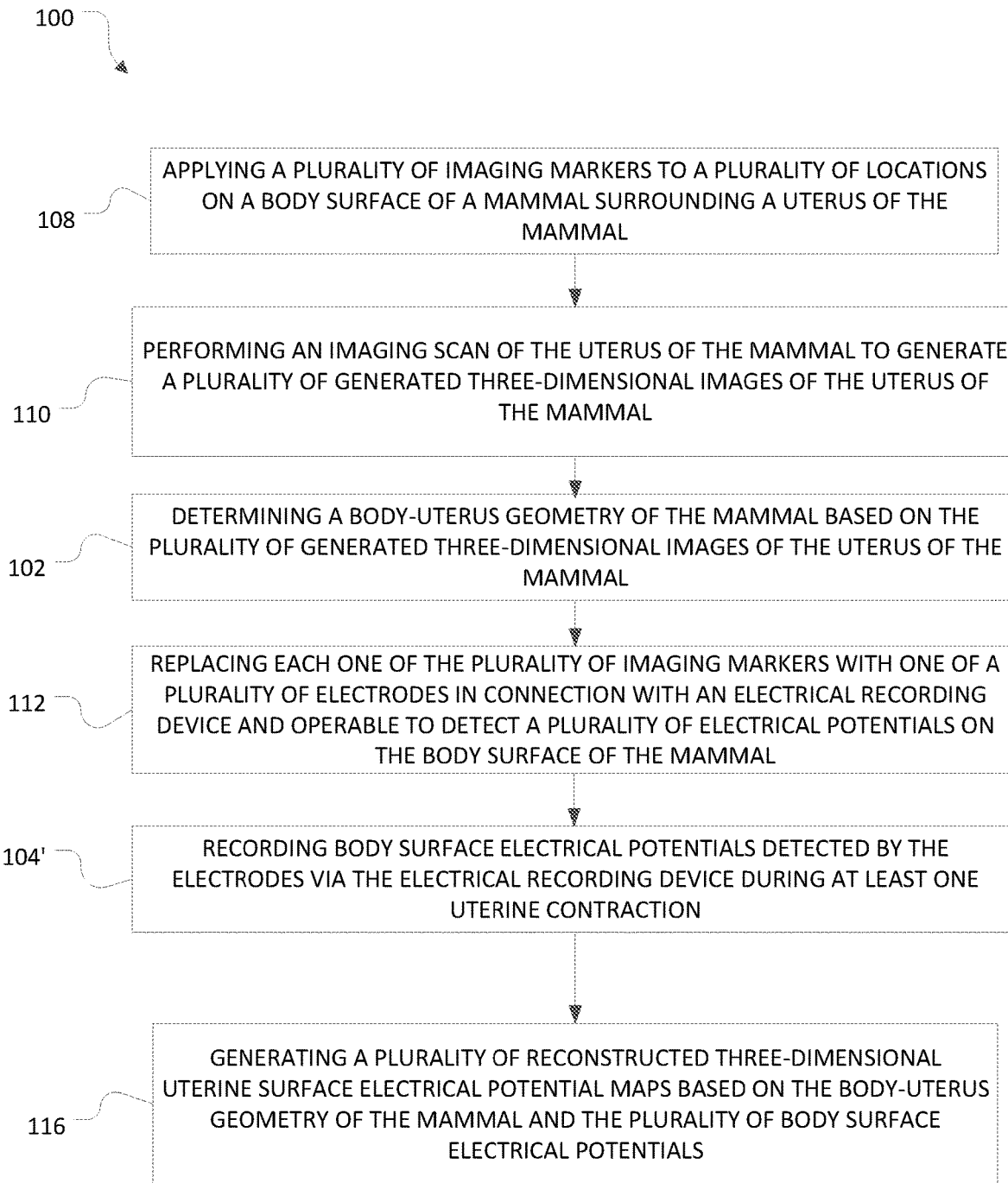
FIG. 1B is a flow diagram showing additional details of the method of FIG. 1A.

A description of a method for noninvasively determining a uterine surface electrical activity of a uterus of a mammal, also referred to as electromyometrial imaging (EMMI), as illustrated in FIGS. 1A and 1B, is first disclosed herein.

The method shown in FIG. 1A is provided by way of example, as there are a variety of ways to carry out the method. Additionally, while the example method is illustrated with a particular order of steps, those of ordinary skill in the art will appreciate that FIG. 1A and the steps shown therein can be executed in any order that accomplishes the technical advantages of the present disclosure and can include fewer or more steps than illustrated. Each step shown in FIG. 1A represents one or more processes, methods or subroutines, carried out in the example method.

Figure 11A:
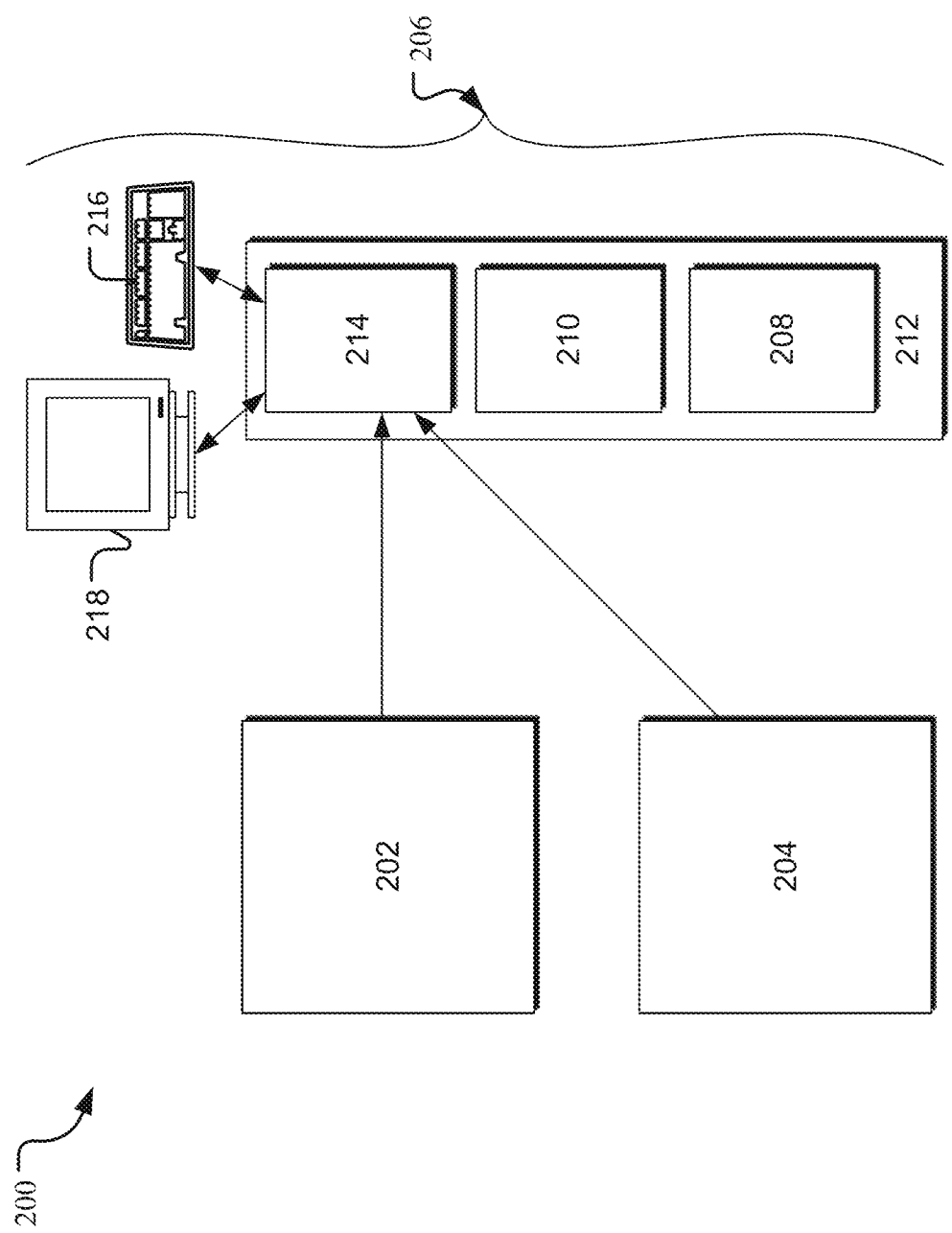
FIG. 11A shows an example system for noninvasively determining uterine electrical activity of a mammal.
Figure 11B:
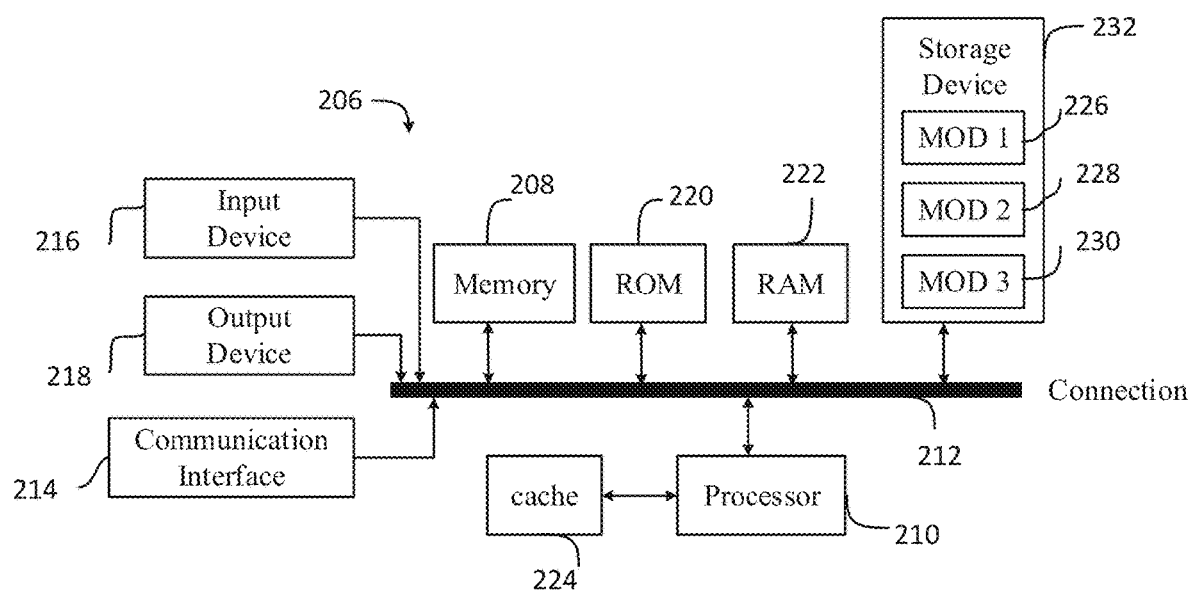
FIG. 11B shows an example computing system of the system of FIG. 11A.

FIG. 1A shows a flow diagram of an example method 100 for noninvasively determining uterine electrophysiology of a uterus of a mammal. Non-limiting examples of the mammal include humans, sheep, cats, and dogs. One or more steps of the method may be performed using at least one of the components of system 200, as seen in FIGS. 11A-11B.

The method 100 can begin at step 102. In method 100, step 102 may include determining a body-uterus geometry of the mammal from a plurality of generated three-dimensional images of the uterus of the mammal. Step 104 may include detecting and recording a plurality of body surface electrical potentials. Step 106 may include determining a uterine surface electrical data by reconstructing the plurality of generated three-dimensional images based on the body-uterus geometry of the mammal and the plurality of body surface electrical potentials.

FIG. 1B illustrates additional details of the method 100. Method 100 may further include steps 108 and 110. The plurality of generated three-dimensional images of the uterus of the mammal that were used to determine the body-uterus geometry in step 102 may be generated via steps 108 and 110.

At step 108, a plurality of imaging markers are applied to a plurality of locations on a body surface of the mammal, wherein the body surface surrounds the uterus. The body surface surrounding the uterus may include an abdomen and a lower back of the mammal. Each one of the plurality of imaging markers is applied to one of the plurality of locations on the body surface. In some examples, the plurality of imaging markers includes a plurality of MRI markers. The number of MRI markers may depend on the application and/or feasibility for each patient. In various examples, the plurality of MRI markers may include up to 50, up to 100, up to 150, up to 200, up to 250, or up to 300 MRI markers. In at least one example, the plurality of MRI markers includes up to about 256 MRI markers.

Figure 10A:
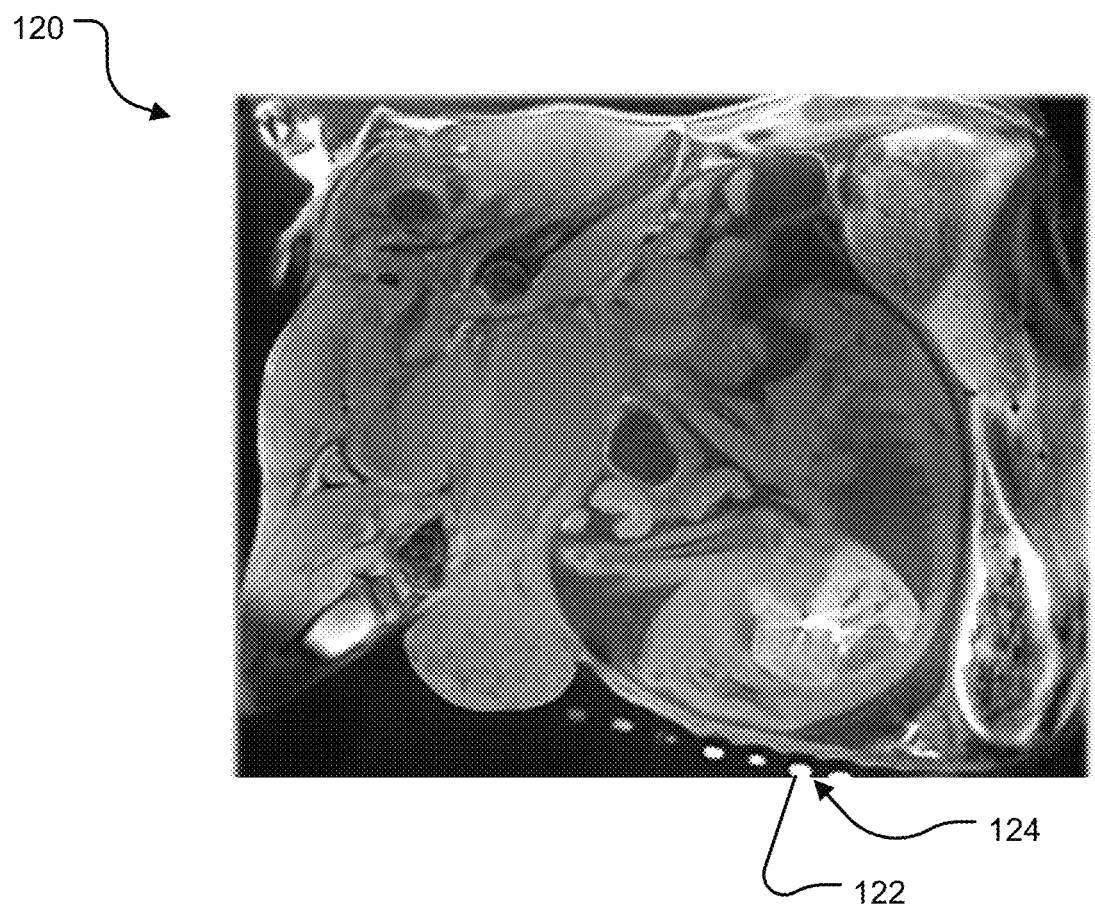
FIG. 10A shows an MRI scan obtained via an example method to generate sheep body geometry.

At step 110, an imaging scan of the uterus of the mammal is performed. The imaging scan is operable to provide the plurality of generated three-dimensional images of the uterus of the mammal. The imaging scan may be any scan performed using an imaging modality that is reasonably safe for imaging a uterus and body surface geometry of a pregnant mammal. Non-limiting examples of imaging scans include MRI scans or ultrasound. In some examples, the imaging scan is an MRI scan and the plurality of generated three-dimensional images includes MRI images. In some examples, at least a portion of the plurality of imaging markers are visible on at least a portion of the plurality of generated three-dimensional images, such as MRI markers 122, visible in FIG. 10A. In such examples, each of the plurality of imaging markers indicate the position of one of the plurality of locations on the body surface. Referring to FIG. 10A, an example MRI scan 120 of a sheep is shown and each of the plurality of MRI markers 122 indicate the position of one of a plurality of locations 124 on a sheep body surface.

Figure 10B:
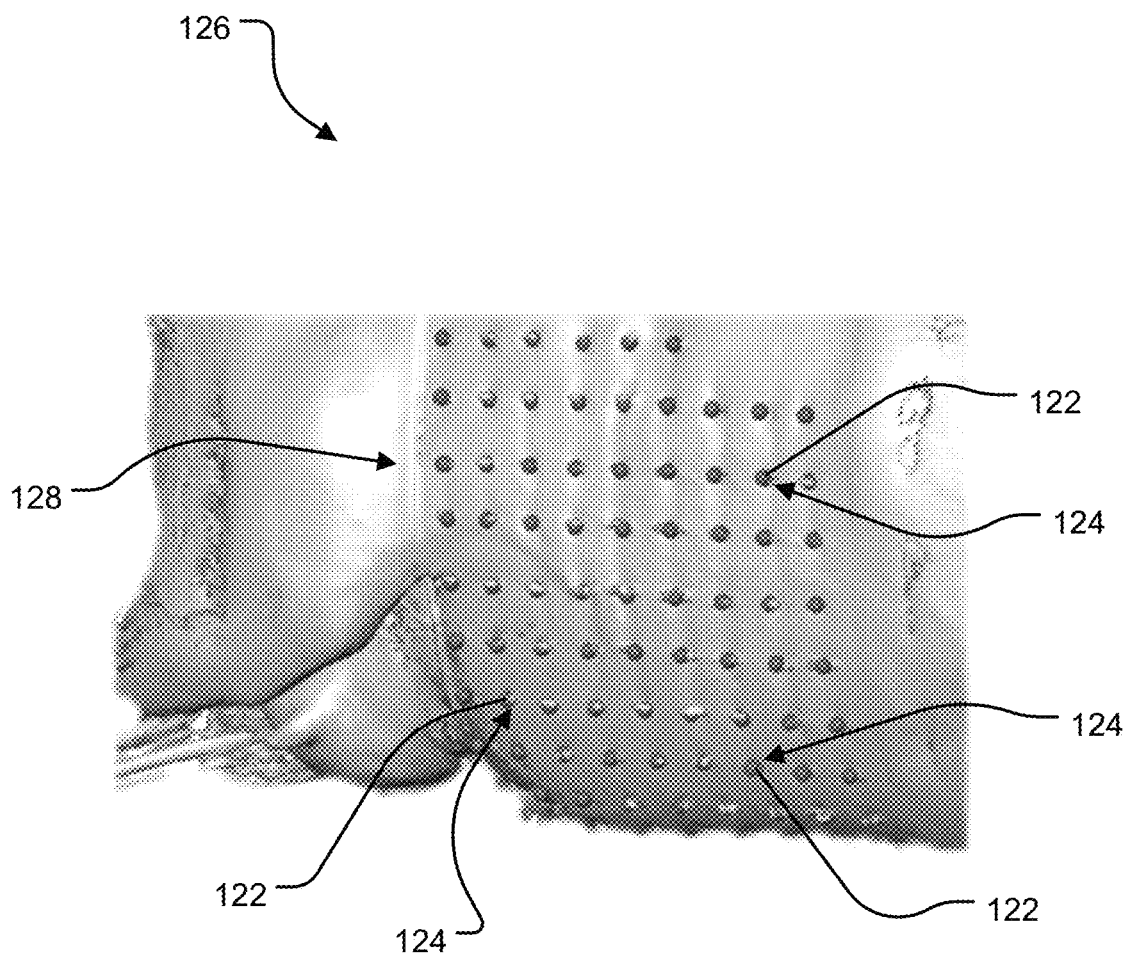
FIG. 10B shows a body surface geometry of a sheep obtained via a noninvasive example method to generate sheep body geometry.

In some examples, determining the body-uterus geometry at step 102 may be performed using at least one of the components of system 200, as seen in FIG. 11A. In some examples, step 102 may include receiving the plurality of generated three-dimensional images at a processor, such as processor 210, wherein the processor is operable to segment the plurality of generated three-dimensional images to generate the body-uterus geometry in response to instructions from a non-transitory computer readable medium. In some examples the processor is in connection with the imaging modality that generated the plurality of generated three-dimensional images. In such examples, at least one processor may be operable to determine a body-uterus geometry of the mammal based on the plurality of imaging markers applied to the body surface surrounding the uterus of the mammal. The body-uterus geometry of the mammal is specific to the individual mammal. In at least one example, the instructions from the non-transitory computer readable medium are instructions encoded in EMMI software. For example, FIG. 10B shows a sheep body surface geometry 126 generated from a plurality of MRI scans, such as MRI scan 120 of FIG. 10A, using the EMMI software. The sheep body surface geometry 126 shows the plurality of MRI markers 122 positioned at the plurality of locations 124 on a body surface 128 of the sheep.

At step 104', the plurality of electrical potentials on the body surface (also referred to as the body surface electrical activity and/or the plurality of electrical signals) are recorded via the electrical recording device (also referred to as the electrical mapping device) during at least one uterine contraction. The electrical mapping device is operable to record the body surface electrical potentials.

Method 100 may include step 112. The body surface electrical potentials referenced in step 104 may be detected via step 112. At step 112, each one of the plurality of imaging markers is replaced with one of a plurality of electrodes. Thus, each one of the plurality of electrodes is applied to one of the plurality of locations on the body surface surrounding the uterus of the mammal. Each one of the plurality of electrodes may be operable to detect a plurality of electrical signals on the body surface surrounding the uterus of the mammal, at the plurality of locations. In some examples, the electrodes include unipolar active electrodes. In some examples, the electrodes are in connection with an electrical mapping device. In some examples, the electrical mapping device is operable to record the body surface electrical potentials at the plurality of locations via a plurality of electrodes. In some examples, the number of the plurality of electrodes is equal to the number of the plurality of MRI markers. The number of electrodes may depend on the application and/or feasibility for each patient. In various examples, the number of electrodes may include up to 50, up to 100, up to 150, up to 200, up to 250, or up to 300 electrodes. In at least one example, the plurality of electrodes includes up to about 256 electrodes.

In some examples, determining the uterine surface electrical data at step 106 may include reconstructing the plurality of generated three-dimensional images to generate a plurality of reconstructed three-dimensional uterine surface electrical potential maps based on the body-uterus geometry of the mammal and the plurality of body surface electrical potentials, as seen in step 116.

Thus, the presently disclosed technology allows determination of the electrical activation patterns of the uterus (i.e., the uterine surface electrical data), via noninvasively obtained data, by combining the detailed body surface electrical activity (i.e., the body surface electrical potentials) with the body-uterus geometry derived from three-dimensional images. This allows the generation and comprehensive evaluation of three-dimensional uterine electrical activation patterns at high spatial and temporal resolution. The plurality of uterine surface electrical potentials recorded in step 116 represent electrical potential distribution over the entire uterine surface during an observation window. This is particularly advantageous because it allows noninvasive monitoring of initiation and propagation of uterine contractions by tracking electrical signals across the entire uterine surface.

In some examples, determining the uterine surface electrical data at step 106 may include reconstructing a plurality of electrograms based on the body-uterus geometry of the mammal and the plurality of body surface electrical potential maps. In such examples, the plurality of electrograms may be generated by assembling a time series of potential values at a given uterine site from the potential maps. The plurality of uterine surface electrical potential maps display electrical potential distribution over the entire uterine surface at a given time point. The plurality of electrograms may also provide temporal features of electrical activity at local sites on the uterine surface.

In some examples, determining the uterine surface electrical data at step 106 may include reconstructing a plurality of isochrones maps based on the body-uterus geometry of the mammal and the plurality of body surface electrical potential maps. In such examples wherein the uterine electrical activity is determined by generating a plurality of isochrones maps, the plurality of isochrones maps may be generated by assembling local activation time of each uterine surface site during an observation window. In such examples, the observation window may be the time period of the at least one uterine contraction, e.g., the observation window may start at a time point when uterine electrical activity started to occur on a previously resting uterus, and the observation window may end at the time point when the uterus returned to electrical quiescence.

In some examples, determining the uterine electrical activity at step 106 includes generating a plurality of uterine surface electrical potential maps, a plurality of electrograms, and/or a plurality of isochrone maps.

In some examples, determining the uterine surface electrical data at step 106 and step 116 may be performed using at least one of the components of system 200, as seen in FIG. 11A. In some examples, step 106 may include deriving the uterus surface geometry from the body-uterus geometry, deriving the uterine surface electrical activity from the body surface electrical activity, and mapping the uterine surface electrical activity onto the uterus geometry, using at least one of the components of system 200, such as processor 210. In such examples, the processor 210 may be operable to perform step 104 in response to instructions from a non-transitory computer readable medium, such as software memory 208. In at least one example, the instructions from the non-transitory computer readable medium are instructions encoded in the EMMI software.

For example, FIG. 10B shows a sheep body surface geometry 126 generated from a plurality of MRI scans, such as MRI scan 120 of FIG. 10A, using the EMMI software. The sheep body surface geometry 126 shows the plurality of MRI markers 122 positioned at the plurality of locations 124 on a body surface 128 of the sheep.

FIGS. 1C-1D illustrate a study performed to assess the accuracy of EMMI, wherein EMMI-reconstructed uterine surface potentials reconstructed via the method of FIG. 1C were qualitatively and quantitatively compared to the measured uterine surface potentials measured via the method of FIG. 1D. FIG. 1C is a flow diagram illustrating additional details of the method of FIG. 1A. In FIG. 1C, MRI scans were acquired and then segmented to generate body-uterus geometry. On the body surface, up to 256 electrodes were placed in the locations of the corresponding MRI markers. Body surface electrograms were recorded and mapped onto body surface potentials. The measured body surface potentials and the body-uterus geometry were combined by EMMI software to generate reconstructed uterine surface potentials (spatial potential distribution on the 3D uterine surface at each instance in time). FIG. 1D is a flow diagram of an example method for uterine electromyography used to assess the accuracy of the method of FIG. 1C. In FIG. 1D, the sheep uterus was surgically exposed, and an elastic sock containing 64 electrodes was slipped over the uterus. An electrical pacing lead (indicated by asterisk) was placed onto the uterine surface. After closing the abdomen, body surface electrodes were placed in their original locations. When pacing the uterus through the pacing lead, the uterine and body surface electrograms were recorded simultaneously. The uterine surface electrograms were directly mapped onto MRI-derived uterine surface to generate measured uterine surface potentials. Finally, the EMMI-reconstructed uterine surface potentials reconstructed via the method of FIG. 1C were qualitatively and quantitatively compared to the measured uterine surface potentials measured via the method of FIG. 1D.

Figure 2A:
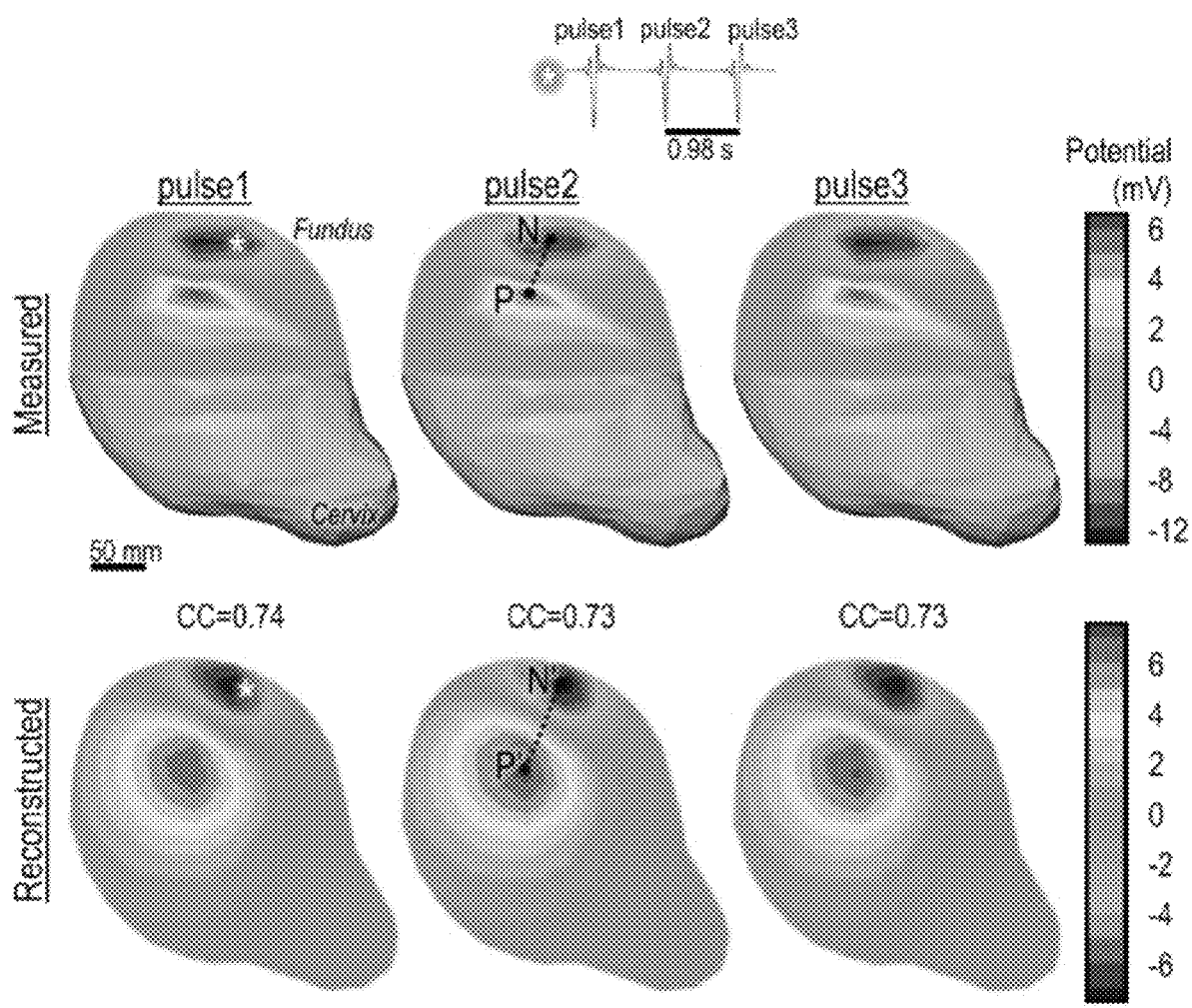
FIG. 2A shows an electrogram from the site of a pacing lead placed in the top segment of the uterus of sheep A and a right lateral view of three-dimensional uterine surface potential maps at the peaks of three pulsing paces for sheep A, reconstructed and measured in a study implementing the methods of FIGS. 1C and 1D, respectively.

FIG. 2A shows an electrogram from the site of a pacing lead placed in the top segment of the uterus of sheep A and a right lateral view of three-dimensional uterine surface potential maps at the peaks of three pulsing paces for sheep A, reconstructed and measured in a study implementing the methods of FIGS. 1C and 1D, respectively.

Figure 2B:
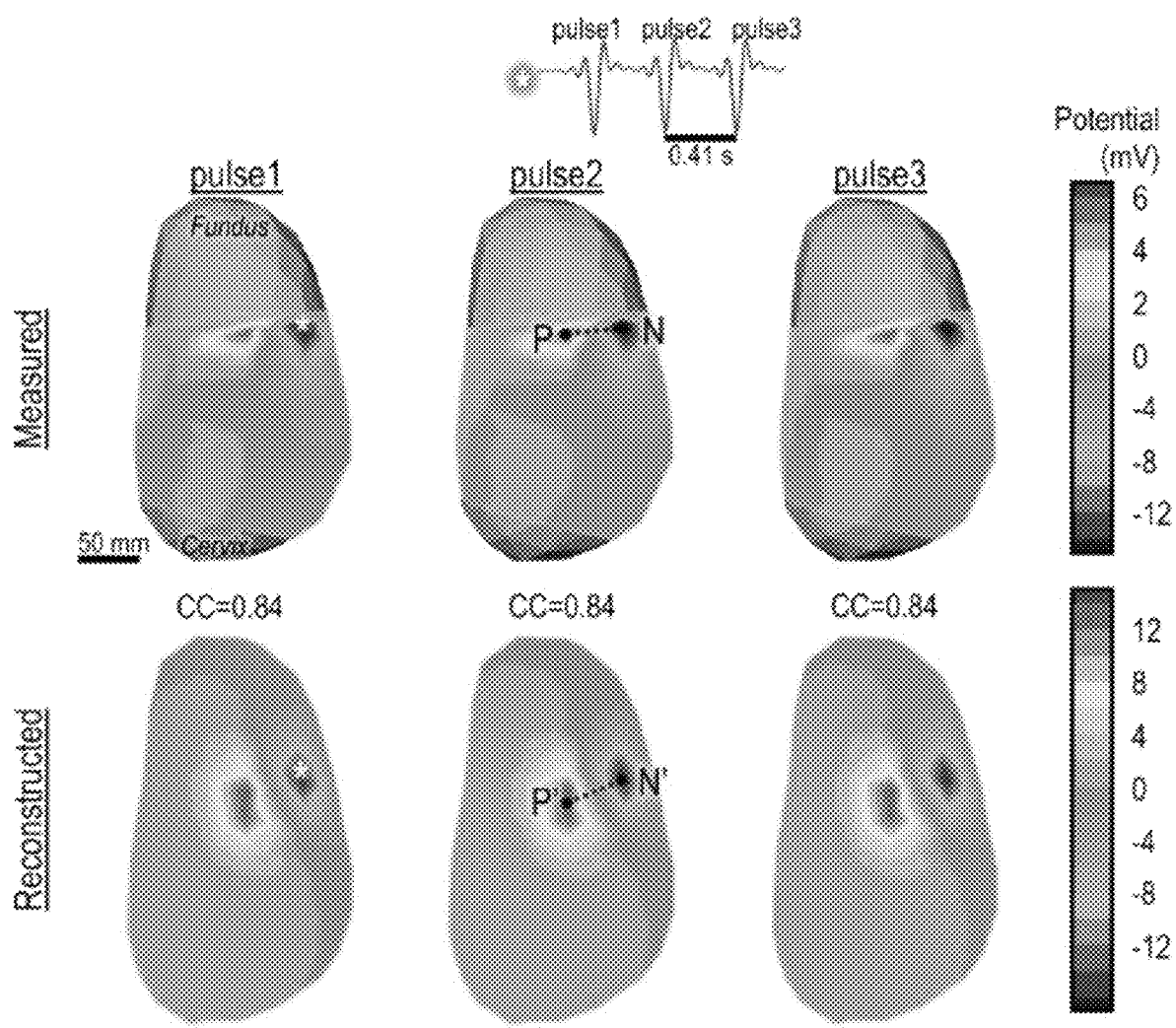
FIG. 2B shows an electrogram from the site of a pacing lead placed in the middle segment of the uterus of sheep B and a right lateral view of three-dimensional uterine surface potential maps at the peaks of three pulsing paces for sheep B, reconstructed and measured in a study implementing the methods of FIGS. 1C and 1D, respectively.

FIG. 2B shows an electrogram from the site of a pacing lead placed in the middle segment of the uterus of sheep B and a right lateral view of three-dimensional uterine surface potential maps at the peaks of three pulsing paces for sheep B, reconstructed and measured in a study implementing the methods of FIGS. 1C and 1D, respectively. N and N' denote negative potential centers in the measured and EMMI-reconstructed potential maps respectively, while P and P' denote positive potential centers in the measured and EMMI-reconstructed potential maps respectively. Dashed lines denote vectors connecting the negative and positive centers. Spatial correlation coefficients (CCs) of the potential maps shown on this figure (defined in Eq. 7) were computed at the peak of each pacing pulse. Distance error of negative and positive potential centers between the measured and EMMI-reconstructed potential maps and CC of potential maps were analyzed during all pacing pulses for sheep A (N=138) for sheep B (N=390), summarized in Table 1 in the examples below.

The disclosure now turns to a system for noninvasively determining uterine surface electrical activity of a mammal. The mammal may have a body surface surrounding a uterus of the mammal.

A description of an example system for noninvasively determining uterine surface electrical activity a mammal, as illustrated in FIG. 11A, is first disclosed herein.

FIG. 11A shows an example system 200 for noninvasively determining uterine electrical activity of a mammal. The system 200 may include the medical imaging modality 202 and the plurality of imaging markers, such as the MRI markers 122. The medical imaging modality 202 may be in connection with a computing system 206. In some examples, the medical imaging modality 202 may be in connection with a communication interface 214 of computing system 206. In some examples, the medical imaging modality 202 may be operable to perform the imaging scan to generate the plurality of generated three-dimensional images of the uterus of the mammal, as seen in FIG. 1B, step 110. In some examples, the medical imaging modality 202 is an imaging modality that is substantially safe for use during pregnancy and is operable to record three-dimensional images of the uterus of the mammal. In some examples, the medical imaging modality 102 may include a magnetic resonance imaging machine (MRI) or an ultrasound machine.

The system 200 may also include an electrical mapping device 204 and electrodes. The electrical mapping device 204 may be in connection with the computing system 206. In some examples, the electrical mapping device 204 may be in connection, via a connection 212, with at least one processor, such as the processor 210 of the computing system 206. The electrical mapping device 204 may be in connection with the electrodes and may be operable to detect the body surface electrical activity of the body surface during at least one contraction and/or during an operation window defined by a start time and a stop time.

The system 200 may further include a computing system having at least one non-transitory computer readable medium. In some examples, the at least one non-transitory computer readable medium may include the system memory 208.

The system 200 may include at least one processor, such as the processor 210. The least one non-transitory computer readable medium, e.g., the system memory 208, may store instructions which when executed by processor 210, to cause processor 210 to perform at least one step. In at least one example, the instructions from the non-transitory computer readable medium are instructions encoded in the EMMI software. In some examples, the instructions may cause the processor 210 to receive data from the medical imaging modality 202 and/or the electrical mapping device 204, such as the plurality of generated three-dimensional images, the plurality of locations, and/or the body surface electrical potentials. In some examples, the instructions may cause the processor 210 to determine a body-uterus geometry of the mammal, such as in step 102 of FIGS. 1A and 1B. In some examples, the instructions may cause the processor 210 to generate a plurality of three-dimensional uterine surface electrical potential maps based on the body-uterus geometry and the plurality of body surface electrical potentials, such as in step 106 of FIG. 1A and step 116 of FIG. 1B.

In some examples, the instructions may cause the processor 210 to derive electrograms and/or isochrones maps from the uterine surface electrical potential maps, such as in step 106 of FIG. 1A.

Referring to FIGS. 11A and 11B, system 200 may include a computing system, such as the computing system 206. FIG. 11B shows an example computing system 206. In some examples computing system 206 is a distributed system in which the functions described in this disclosure can be distributed within a datacenter, multiple datacenters, a peer network, throughout layers of a fog network, etc. In some examples, one or more of the described system components represents many such components each performing some or all of the function for which the component is described. In some examples, the components can be physical or virtual devices.

The computing system 206 may include a connection 212 by which components of system 200 are in communication with each other. Connection 212 can be a physical connection via a bus, or a direct connection into processor 210, such as in a chipset or system-on-chip architecture. Connection 212 can also be a virtual connection, networked connection, or logical connection.

Also included in the computing system 206 are the at least one processing unit (CPU or processor) 210 and various system components coupled via the connection 212, including system memory 208, read only memory (ROM) 220 or random access memory (RAM) 222 to processor 210. Computing system 206 can include a cache of high-speed memory 224 connected directly with, in close proximity to, or integrated as part of processor 210.

Processor 210 can include any general purpose processor and a hardware service or software service, such as services (e.g. MOD 1 226, MOD 2 228, and MOD 3 230) stored in storage device 232, operable to control processor 210 as well as a special-purpose processor where software instructions are incorporated into the actual processor design. Processor 210 may essentially be a completely self-contained computing system, containing multiple cores or processors, a bus, memory controller, cache, etc. A multi-core processor may be symmetric or asymmetric.

To enable user interaction, computing system 206 includes an input device 216, as seen in FIGS. 11A and 11B, which can represent any number of input mechanisms, such as a microphone for speech, a touch-sensitive screen for gesture or graphical input, keyboard, mouse, motion input, speech, etc. Computing system 206 can also include output device 218, as seen in FIGS. 11A and 11B, which can be one or more of a number of output mechanisms known to those of skill in the art. In some instances, multimodal systems can enable a user to provide multiple types of input/output to communicate with computing system 206. Computing system 206 can include the communications interface 214, which can generally govern and manage the user input and system output, and also connect computing system 206 to other nodes in a network. In some examples, the output device 218 may include a display monitor operable to exhibit the uterine surface electrical activity, such as uterine surface electrical potential maps, generated at step 106 of FIG. 1A. In such examples, the display can allow for improved monitoring of uterine contractions by facilitating the comprehensive evaluation of three-dimensional uterine electrical activation patterns at high spatial and temporal resolution in real or near-to-real time. There is no restriction on operating on any particular hardware arrangement and therefore the basic features here may easily be substituted for improved hardware or firmware arrangements as they are developed.

Storage device 232 can be a non-volatile memory device and can be a hard disk or other types of computer readable media which can store data that are accessible by a computer, such as magnetic cassettes, flash memory cards, solid state memory devices, digital versatile disks, cartridges, battery backed random access memories (RAMs), read only memory (ROM), and/or some combination of these devices.

The storage device 232 can include software services, servers, services, etc., that when the code that defines such software is executed by the processor 210, it causes the system to perform a function. In some examples, a hardware service that performs a particular function can include the software component stored in a computer-readable medium in connection with the necessary hardware components, such as processor 210, connection 212, output device 218, etc., to carry out the function.

EXAMPLES

Example 1: Study Design

In the study herein described, a term pregnant sheep model was used to show that EMMI provided accurate measurements, as uterine surface electrical potential maps reconstructed from body surface potentials, matched those measured from electrodes placed directly on the uterus during electrical pacing. Next, it was shown that EMMI could robustly reconstruct uterine electrical activation maps during oxytocin-induced contractions, even in the presence of simulated Gaussian noise and geometric deformations. Finally, it was shown that EMMI is feasible, as it could be used to noninvasively map induced uterine contractions.

In the study, to create a three-dimensional subject-specific body-uterus geometry, MRI was performed after applying up to 256 MRI markers to the subject's body surface around the abdomen and lower back. When the subject was in labor, the MRI markers were replaced with body surface electrodes in the same locations, and multi-channel body surface potentials were simultaneously recorded with a portable electrical mapping device. Finally, as was done in ECGI, EMMI software employed the method of fundamental solution to solve Laplacian partial differential equations, and combine electrical signals with the uterus geometry to generate uterine surface potential maps (electrical activity across the uterus at a single time point) (as seen in FIG. 1C). These maps were used to derive electrograms (electrical waveforms over time at each uterine site) and isochrone maps (time of activation at each point across the entire uterus surface).

This study was designed to develop EMMI and validate its capability to noninvasively image the three-dimensional electrical activation patterns during uterine contractions. In order to achieve this goal, a pregnant sheep model was first employed to simultaneously record the electrical potentials from body surface electrodes and uterine surface electrodes. EMMI's accuracy was validated by comparing the EMMI-reconstructed uterine potential maps to those measured directly from the uterine surface during the pacing episodes. Next, EMMI's robustness of reconstructing uterine electrical activation in circumstances that would be experienced clinically was investigated. Specifically, EMMI-reconstruct uterine electrical activation maps during oxytocin-induced contractions, even in the presence of simulated Gaussian noise and geometry deformations, was evaluated. Finally, EMMI's feasibility, as it can be used to noninvasively map uterine contractions in humans was evaluated.

Example 2: Sheep Model

To test EMMI, Katandin sheep were used, which are a good model for human pregnancy because they have a similar abdomen size as humans. Additionally, properly timed steroid injections can be used to induce sheep labor. Although sheep have a bipartite uterus, a single newborn offspring is of similar weight to a human baby. Nine near-term pregnant Katandin sheep were used (which have less lanolin skin secretions than other breeds); the first three sheep were used as pilot animals to develop MRI sequences and experimental protocols, and the remaining six sheep were used for electrical recordings. Data was excluded from one sheep that had twins and the remaining five sheep were used to assess the accuracy, robustness, and feasibility of EMMI.

Katandin sheep (Francis Sheep Farm, an institutionally approved vendor) were obtained between gestation days 140 and 145 (on average, this breed delivers lambs around day 147) of their first or second pregnancies. Dexamethasone (16 mg intramuscular)) was administered 24 to 48 hours before the MRI to sensitize the uterine response to oxytocin. Sheep were fasted before anesthesia and on the day of the study. Sheep were anesthetized with 10 mg/kg intramuscular ketamine and isoflurane by mask, and animals were maintained under isoflurane anesthesia during the MRI and surgical procedure. Sheep were shaved free of hair circumferentially from the midthorax to the level of the pelvis.

Example 3: MRI Scan

MRI markers were applied externally around the lower abdomen and back of the sheep. MRI (without any contrast agent) was performed on a 3T Siemens PRISMA using a Radial Volume Interpolated Breath-hold Examination fast T1-weighted sequence with spatial resolution of 1 mm×1 mm×3 mm. Localizer was used to adjust the field of view to cover the entire sheep uterus and cervix. Then, sheep were scanned along the axial direction for about 135-200 slices, depending on the size of the sheep.

Example 4: Surgery and Electrical Recording

Figure 10C:
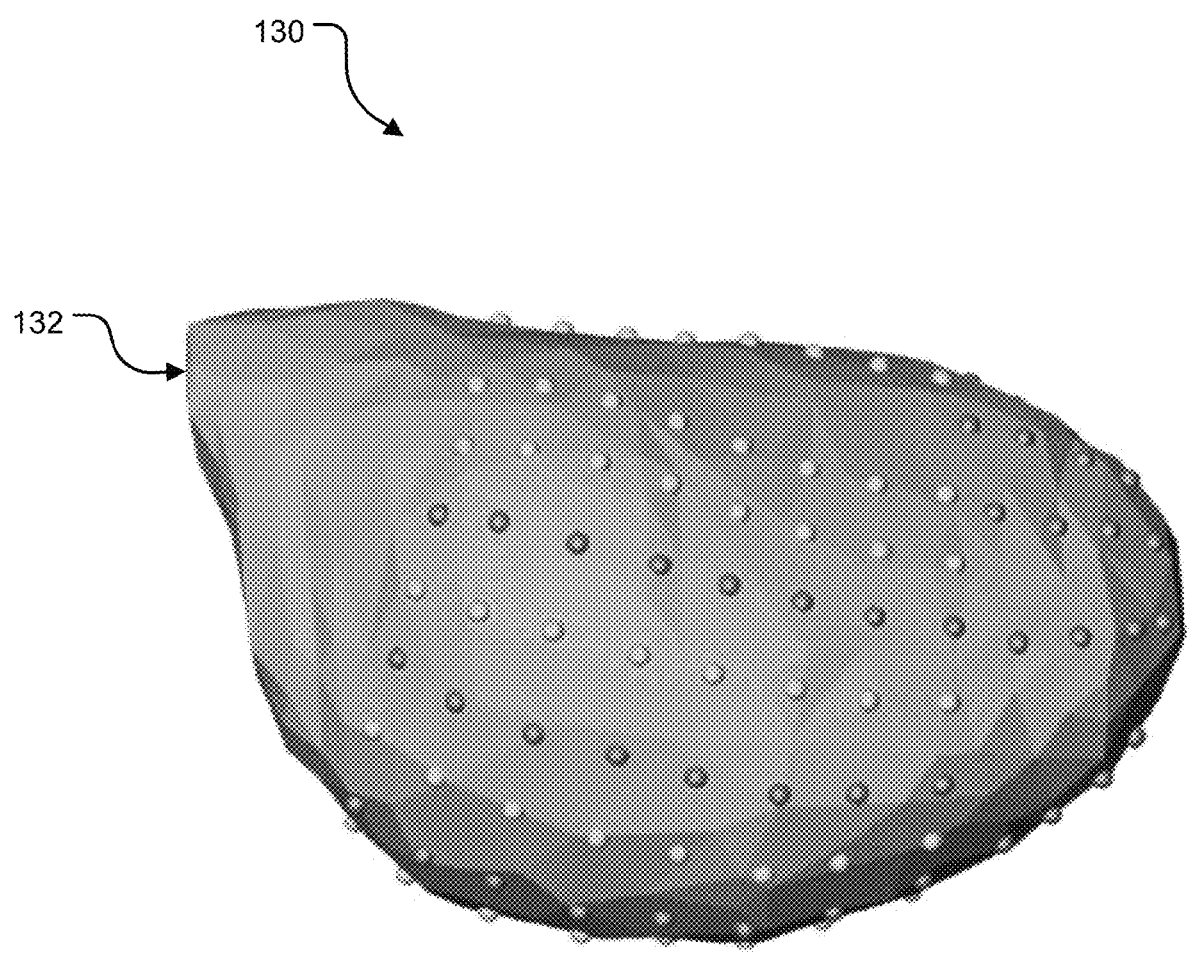
FIG. 10C shows a sheep uterine surface geometry of a sheep uterine surface obtained via an invasive method to generate sheep uterine surface.
Figure 10D:
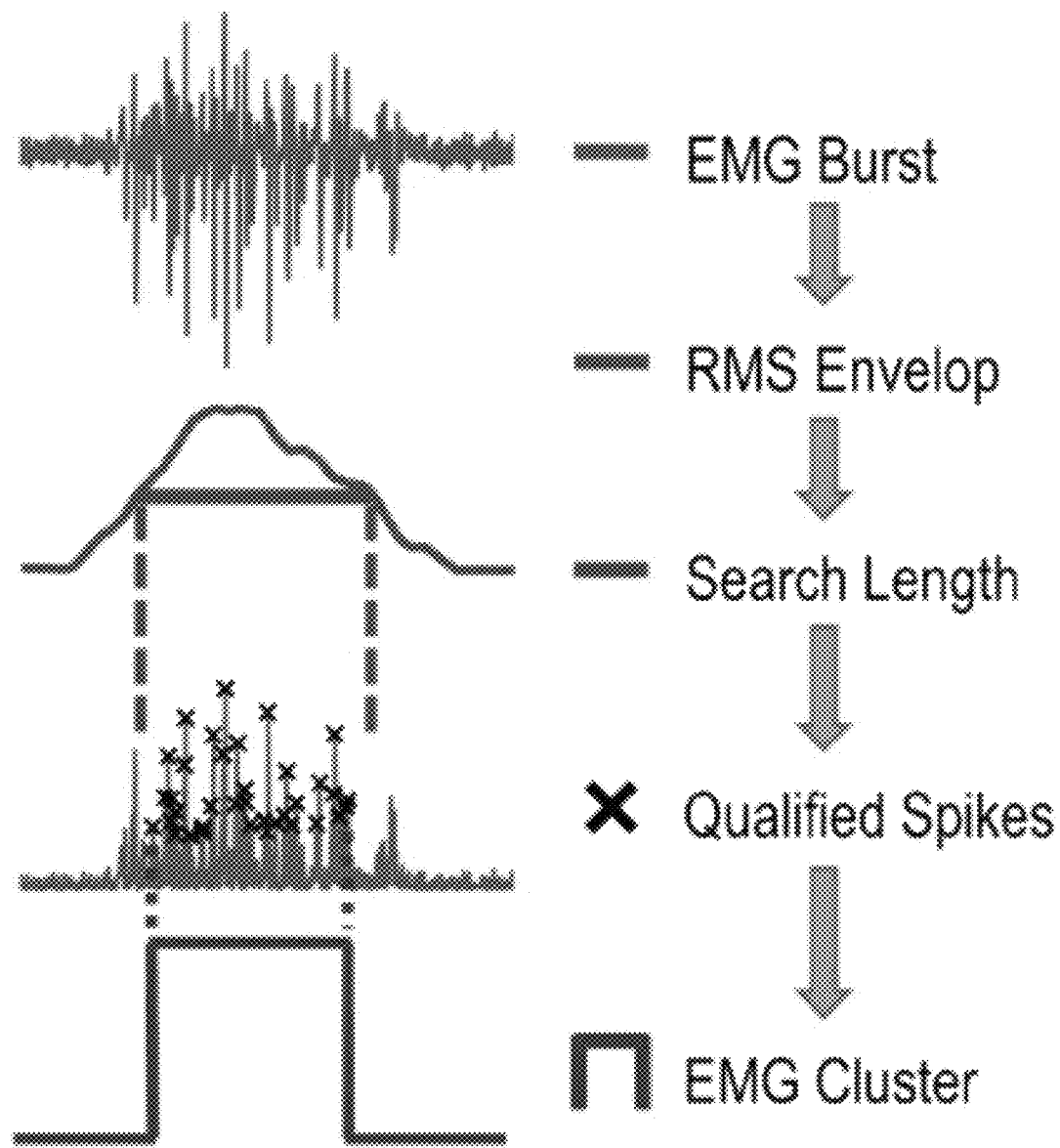
FIG. 10D illustrates a steps of an example method to identify EMG burst clusters in electrograms.

Within one hour after the MRI, the sheep was brought to the operating room and placed in left lateral recumbency. Multiple oxytocin boluses (10-20 units intravenously) were delivered to the sheep, and uterine contractions were monitored by TOCO readings. The body surface MRI markers were removed and replaced with unipolar active electrodes in corresponding locations. For the EMMI feasibility study, up to 256 body surface electrodes were connected to a BioSemi portable acquisition system (BioSemi) for noninvasive body surface electrical recording during oxytocin-induced uterine contraction about 15-40 minutes before surgery. The system sampled active electrodes at 2048 Hz with 24-bit resolution. To accommodate the paralumbar surgical approach, body surface electrodes were retracted dorsal and ventral. Lidocaine was infiltrated subcutaneously to create a local line block, and an incision was made in the right lateral paralumbar fossa. Upon entering the abdomen, the uterus 130 was identified and exteriorized such that a proprietary electrode sock could be placed on the uterine surface. Oxytocin-induced uterine contractions were visually confirmed by two obstetricians and one veterinary surgeon. Unipolar pin-type active electrodes were inserted into electrode holders in the sock, and in direct contact with the uterine surface. The sock was placed such that one column of electrodes was in line with the fetus's spine. The positions of the electrodes were recorded as described in FIGS. 10A-10C. For sheep A and B, a cardiac pacing lead (controlled by a Medtronic 5375 Pulse Generator) was placed near one of the electrodes and in direct contact with the uterine surface 132. Next, the uterus was replaced in a normal anatomic position, and the abdomen was closed in layers. The sheep was repositioned into a prone position, and body surface electrodes were repositioned in their previous locations. Then, body surface and uterine surface electrodes were connected to a BioSemi portable acquisition system and simultaneously sampled for about 30 minutes. For assessing EMMI accuracy, the pacing signal was an electrical pulse train with about 0.5 or 1 second between pulses. For assessing EMMI robustness, all body surface electrodes were disconnected and only uterine surface electrodes were used to record uterine surface potentials. After data collection was completed, the ewe and the fetus were euthanized, and all electrodes were removed, sterilized, and reused.

Example 5: Bioelectric-Field Computation

Under the assumption of an electro-quasistatic problem and absence of an electrical source in the volume conductor, the Laplace equation (Eq. 1) was used to describe the electro-quasistatic field. The uterine and body surfaces were the boundaries encompassing the volume conductor as a multiple-connected domain. By defining the measured uterine surface electrical potentials as the Dirichlet boundary condition (Eq. 2), and by using the known zero Neumann boundary condition (Eq. 3) on the body surface due to the electrical isolation effect of air, body surface potentials could be obtained by solving the Laplace equation:

$$\nabla^2 \varphi(x) = 0, x \in \Omega \quad \text{(Eq. 1)}$$

$$\text{Dirichlet condition } \varphi(x) = \varphi_U(x), x \in \Gamma_U \quad \text{(Eq. 2)}$$

$$\text{Neumann condition } \frac{\partial \varphi(x)}{\partial n} = 0, x \in \Gamma_B \quad \text{(Eq. 3)}$$

where $\Omega$ is the 3D volume between the body surface $\Gamma_B$ and the uterine surface $\Gamma_U$. The volume $\Omega$ is assumed to be homogeneous. $\varphi(x)$ represents the potential at location x. $\varphi_U(x)$ represents the potential on the uterine surface.

$$\frac{\partial \varphi(x)}{\partial n}$$

represents the normal derivative of the potential on the body surface, which equals zero because the body surface $\Gamma_B$ separates the conductive volume $\Omega$ and the non-conductive air outside of volume $\Omega$ Similar to the validation work in ECGI, the Boundary Element Method was used to discretize the Dirichlet and Neumann conditions and the Laplacian equation. After discretization, body surface potentials ($\Phi_B$) can be related with uterine surface potentials ($\Phi_U$) through a linear matrix A, as Eq. 4. A is the transfer matrix encoding the body-uterus geometrical relationship. Because the boundary conditions were known on both boundaries, the computation was well-posed, stable, and accurate.

$$\Phi_B = A\Phi_U \qquad \text{(Eq. 4)}$$

Example 6: Noise and Geometric Deformation

For EMMI robustness evaluation, Gaussian noise was added(10% in signal amplitude) into the computed body surface potentials (Eq. 5). Also added, was random Gaussian-distributed geometric error (3 times standard deviation=1 cm) to both the uterus and body surface geometries.

Example 7: EMMI Inverse Computation

In the inverse computation, under the same assumption as the bioelectric field computation, the Laplace equation governs the 3D electro-quasistatic field (Eq. 1). Body surface electrical activities were measured by a multi-channel electrical mapping system using the Dirichlet boundary condition (Eq. 5) and the known zero Neumann boundary condition (Eq. 6) on the body surface.

$$\text{Dirichlet condition } \varphi'(x) = \varphi_B(x) + \varphi_N(x), x \in \Gamma_B \qquad \text{(Eq. 5)}$$

$$\text{Neumann condition } \frac{\partial \varphi'(x)}{\partial n} = 0, x \in \Gamma_B \qquad \text{(Eq. 6)}$$

where $\varphi_B(x)$ represents the potential on the body surface and $\varphi_N(x)$ represents the Gaussian noise added to $\varphi_B(x)$ on the body surface. To solve the inverse problem of EMMI, the Method of Fundamental Solution (MFS) was used to discretize the Laplacian equation as well as Dirichlet and Neumann conditions as described by Eq. 5 and Eq. 6. MFS was accurate for solving inverse bioelectric field problems in other systems. Because boundary conditions are known on the body surface and no boundary conditions are known on the uterine surface, the EMMI computation involves the inverse of a highly ill-conditioned matrix. To obtain a stable inverse potential solution on the uterine surface $\varphi'(x)$, $x \in \Gamma_U$, zeroth order Tikhonov regularization was used. The degree of regularization was determined by the Composite Residual and Smoothing Operator method (CRESO). Specifically, a scaled mean CRESO parameter was used.

Example 8: EMMI Robustness Evaluation

Figure 3:
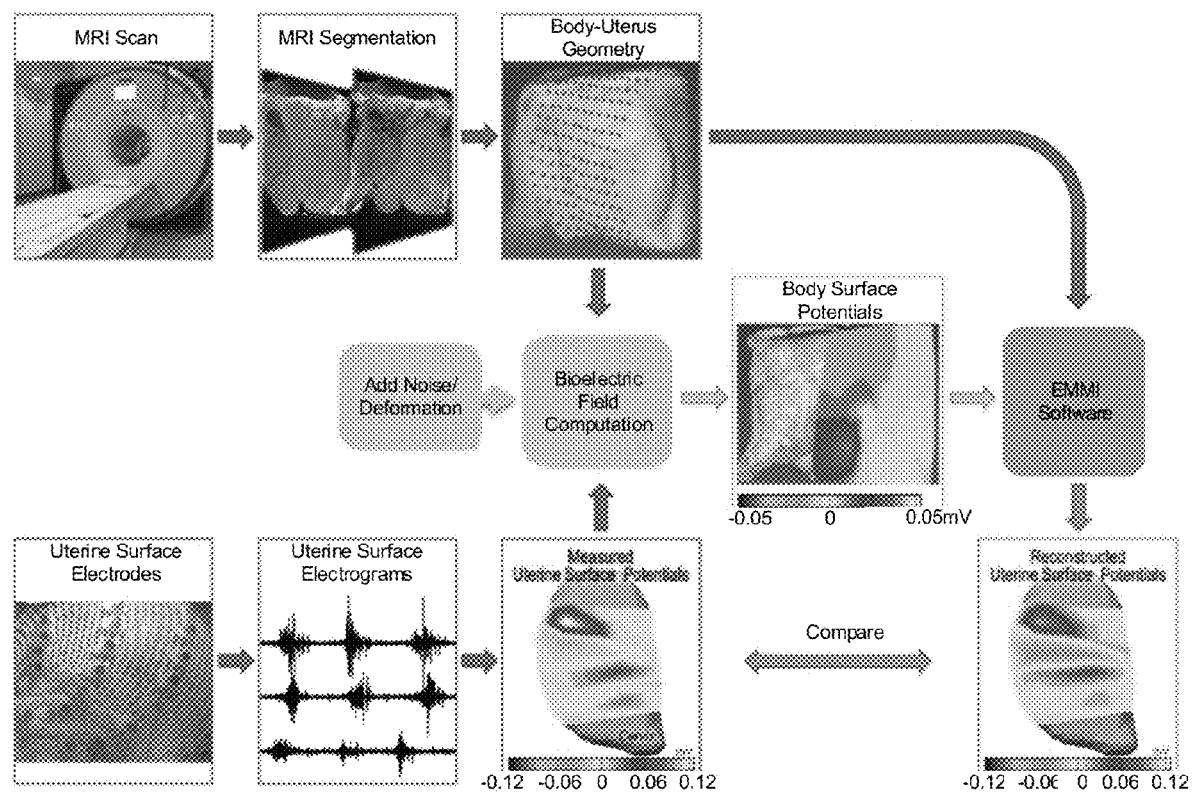
FIG. 3 is a flow diagram illustrating a study performed to assess the robustness of EMMI-reconstructed images, including electrograms, potential maps, and isochrones maps.

FIG. 3 illustrates a study performed to assess EMMI robustness. MRI scans were acquired to provide body-uterus geometry. Next, the uterus was surgically exposed, and an elastic sock containing up to 128 electrodes was slipped over the uterus and used to directly record uterine surface potentials when the sheep was in labor. Oxytocin-induced uterine contractions were visually confirmed by two obstetricians and one veterinary surgeon. The uterine surface potentials were recorded at 2048 Hz sampling rate. Next, adding noise, deformation, or both combined in bioelectric field computation, the body-uterus geometry and experimentally measured uterine surface potentials were used to generate the body surface potentials. For this process, the boundary element method was used to discretize bioelectric field equations. The following were added: 1) Gaussian noise (10% in amplitude) into the computed body surface potentials, 2) Gaussian-distributed geometric error (up to 1 cm over all of the surface) to both the uterus and body surface geometries, or 3) both 10% noise and maximal 1 cm deformation. Next, EMMI was used(which uses the method of fundamental solution), to reconstruct uterine surface potential maps from the forward computed body surface maps. Finally, measured and EMMI-reconstructed uterine data were compared in terms of electrograms, potential maps, and activation isochrones.

Example 9: Processing of Potential Maps, Electrograms, and Isochrone Maps

Upon completing the EMMI inverse computation, uterine surface potential maps were generated, which display potential distribution over the entire uterine surface at a given time point. An electrogram provides temporal features of electrical activity at a local site on the uterine surface and was generated by assembling a time series of potential values at a given uterine site from the potential maps. An isochrone was generated by assembling local activation time of each uterine surface site during an observation window. The start of an observation window was selected as the time point when uterine electrical activity started to occur on a previously resting uterus, and the end of an observation window was selected as the time point when the uterus returned to electrical quiescence.

Example 10: Statistical Analysis

In this study, Pearson correlation-coefficients (CC) and relative error (RE) were employed to quantify accuracy of EMMI-reconstructed uterine surface potentials, electrograms and isochrone maps. CC and RE have been well accepted and used in ECGI studies.

The EMMI-reconstructed uterine surface potentials were compared to the measured uterine surface potentials by calculating the correlation coefficient (CC) and relative error (RE). The equations defining CC and RE are as follows:

$$CC = \frac{\sum_{i=1}^{L}\left(V_i^M - \overline{V^M}\right)\left(V_i^R - \overline{V^R}\right)}{\sqrt{\sum_{i=1}^{L}\left(V_i^M - \overline{V^M}\right)^2}\sqrt{\sum_{i=1}^{L}\left(V_i^R - \overline{V^R}\right)^2}} \qquad \text{(Eq. 7)}$$

$$RE = \sqrt{\frac{\sum_{i=1}^{L}(V_i^R - V_i^M)^2}{\sum_{i=1}^{L}(V_i^M)^2}} \qquad \text{(Eq. 8)}$$

CC is a statistical measure calculating the strength of the relationship between two variables. The range of CC values is between −1.0 to 1.0. A CC of −1.0 indicates a perfect negative correlation, while a CC of 1.0 indicates a perfect positive correlation. A CC of 0.0 indicates no relationship between the two variables. RE is a statistical measure of precision, defined as the ratio of the absolute error of a measurement to the measurement being examined. RE is dimensionless and expressed as a percentage.

For electrograms, temporal CC and RE were calculated. L represents the number of sample points over time at which potentials were measured and reconstructed. $V_i^M$ and $V_i^R$ represent the measured and reconstructed potentials, respectively, at the ith sample point. $\overline{V^M}$ and $\overline{V^R}$ represent the temporal average of the measured and reconstructed potentials, respectively.

For potential maps and isochrone maps, spatial CC and RE were calculated. L represents the number of uterine sites at which potentials were measured and reconstructed. $V_i^M$ and $V_i^R$ represent the measured and reconstructed potentials, respectively, at the ith uterine site. $\overline{V^M}$ and $\overline{V^R}$ represent the spatial average of the measured and reconstructed potentials, respectively. In this analysis, reconstructed potential maps during contractions or pacing pulses were compare with corresponding measured uterine potentials, and reconstructed isochrone maps were compared with corresponding measured isochrone maps. Wilcoxon rank sum test was performed to test the difference in the spatial resolution of measured data and EMMI reconstruction.

Example 11: EMMI Accuracy

To assess EMMI accuracy, a scheme was used that was similar to that used to validate ECGI, in which the epicardial potentials measured from an animal heart were compared to those reconstructed from body surface potentials measured from a human-torso-shaped tank in which the animal heart was suspended. MRI was performed on the anesthetized sheep wearing MRI markers around the lower abdomen and back (FIG. 1C) to generate a body-uterus geometry. The uterus was surgically exposed, an elastic sock was slipped onto the uterus containing 64 electrodes, a cardiac pacing lead was placed directly on the uterine surface through the sock, and the uterus was returned to its original location. After closing the abdomen, 192 electrodes were placed on the body surface in the same position as the MRI markers. While the uterus was paced with a well-controlled electric pulse from the pacing lead, electrical potentials were simultaneously recorded from body surface electrodes and uterine surface electrodes. EMMI software was then used to reconstruct uterine surface potential maps from the body surface potentials and MRI-derived body-uterus geometry. Finally, the reconstructed uterine surface potential maps were compared with those measured directly from the uterine surface during the pacing episodes (FIGS. 1C and 1D).

A total of 118 independent pacing pulses from two sheep were recorded. The pacing lead (indicated by an asterisk in FIGS. 2A and 2B) was placed in the top segment of the uterus near the fundus in sheep A (FIG. 2A) and in the middle segment of the uterus in sheep B (FIG. 2B). FIGS. 2A-2B shows measured and EMMI-reconstructed uterine surface potential maps in a right lateral view during three independent pacing pulses for sheep A (FIG. 2A) and sheep B (FIG. 2B). In these maps, each generated at a specific point in time, warm colors denote positive potentials and cool colors denote negative potentials. The measured potential maps only cover part of the uterine surface because of the limited number of sock electrodes. In contrast, the EMMI-reconstructed uterine surface potential maps (generated from the body surface potentials) represent the potential distribution pattern of the entire uterus. The mean electrode spacing in the measured potential maps was 47±21 (standard deviation) mm for sheep A and 48±18 mm for sheep B. The mean reconstruction point spacing in the EMMI-reconstructed uterine surface potential maps was 31±8 mm for sheep A and 32±7 mm for sheep B. The null hypothesis that the spatial resolution of EMMI reconstruction is same with measured spatial resolution was rejected by Wilcoxon rank sum test with the p<2.2×10$^{-16}$. It is also noted that in the measured potential maps, there were interpolation (triangle shaped) artifacts due to limited number of sock electrodes.

In both the directly measured and the EMMI-reconstructed uterine surface potential maps, it was observed negative potential centers (labeled as N and N' in FIGS. 2A and 2B) adjacent to the pacing leads (white asterisk in FIGS. 2A and 2B). Additionally, it was observed nearby positive potential centers (labeled as P and P' in FIGS. 2A and 2B). These potential centers were in similar locations in the measured and EMMI-reconstructed potential maps. Specifically, in sheep A (FIG. 2A), the negative and positive potential centers differed by 16.5±7.2 mm (mean±standard deviation) and 28.8±11.4 mm, respectively between the measured and EMMI-reconstructed potential maps, and the angles of the vectors connecting the negative and positive centers differed by 6.1±6.5° (N=138, from 30 pacing pulses). Similarly, in sheep B (FIG. 2B), the negative and positive potential centers differed by 2.9±0.0 mm and 8.1±6.3 mm, respectively between the measured and EMMI-reconstructed potential maps, and the angles of the vectors connecting two centers differed by 7.5±8.2° (N=390, from 78 pacing pulses).

To quantitatively assess EMMI reconstruction accuracy, it was calculated correlation coefficients (CCs) (see Eq. 7) between measured and EMMI-reconstructed uterine surface potential maps. In this case, CC values reflect the correlation between measured and EMMI-reconstructed potentials at a single time point for 62 electrode sites in sheep A and 49 electrode sites in sheep B (64 electrodes were placed on the uterus in both sheep, but data from 2 electrodes in sheep A and 15 electrodes in sheep B were discarded owing to poor electrical contact with the uterus). CC is bounded between 0 and 1, with high similarity closer to 1 and low similarity closer to 0. Potential map CC values had median of 0.71 [first quartile (Q1)=0.67, third quartile (Q3)=0.74] for sheep A (N=138) and 0.83 [0.81, 0.84] for sheep B (N=390). CC values suggest that EMMI could accurately reconstruct uterine surface potential maps from body surface potentials during uterine pacing in sheep.

Example 3: EMMI Robustness

Next, the study sought to determine how robustly EMMI could measure uterine electrical activation in circumstances that would be experienced clinically. Specifically, could EMMI measure oxytocin-induced contractions, and would the EMMI reconstruction be negatively affected by maternal or fetal movement that is likely to occur after the MRI but before or during the electrical recording? Additionally, would the EMMI reconstruction be affected by electrical noise in the recording room, such as that produced by nearby equipment? To answer these questions, the study employed a scheme (FIG. 3), similar to a well-established scheme used to validate ECGI, to evaluate the robustness of EMMI electrogram, potential map and isochrone maps. MRI scans were acquired to provide body-uterus geometry. Next, the uterus was surgically exposed, and an elastic sock containing up to 128 electrodes was slipped over the uterus. The uterine surface potentials were recorded at 2048 Hz sampling rate. Next, adding noise, deformation, or both combined in bioelectric field computation, the body-uterus geometry and experimentally measured uterine surface potentials were used to generate the body surface potentials. EMMI software was then used to reconstruct uterine surface potentials. Finally, the EMMI-reconstructed and measured uterine surface potentials were compared.

Example 13: EMMI Electrogram

Figure 4A:
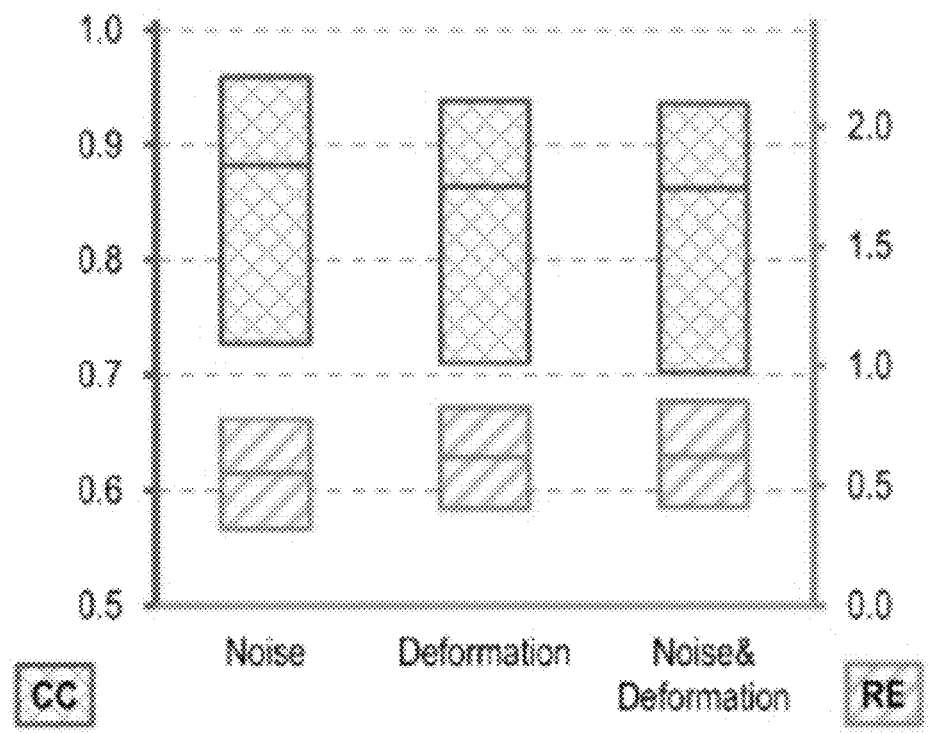
FIG. 4A is a box plot of correlation coefficients (CCs, blue, diamond checkered pattern, defined in Eq. 7) and relative errors (REs, orange, diagonal pattern, Eq. 8) comparing EMMI-reconstructed uterine surface electrograms with measured uterine surface electrograms under the indicated conditions (N=52)
Figure 4B:
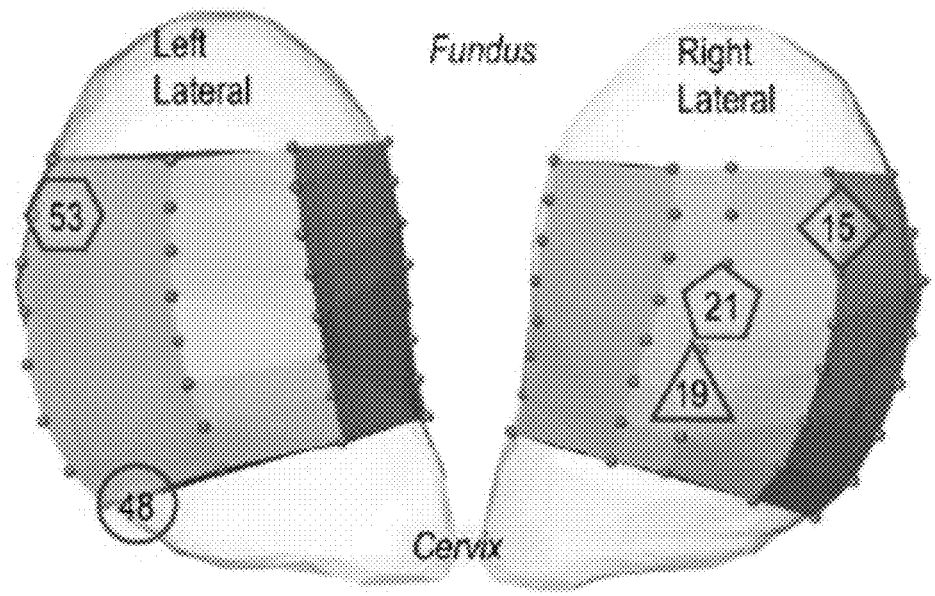
FIG. 4B shows a left and right lateral view of EMMI-reconstructed surface electrograms of a sheep uterus wherein the numbers differentiated by various shapes indicate the discrete uterine surface sites where measured and reconstructed uterine surface electrograms are compared in FIG. 4C.
Figure 4C:
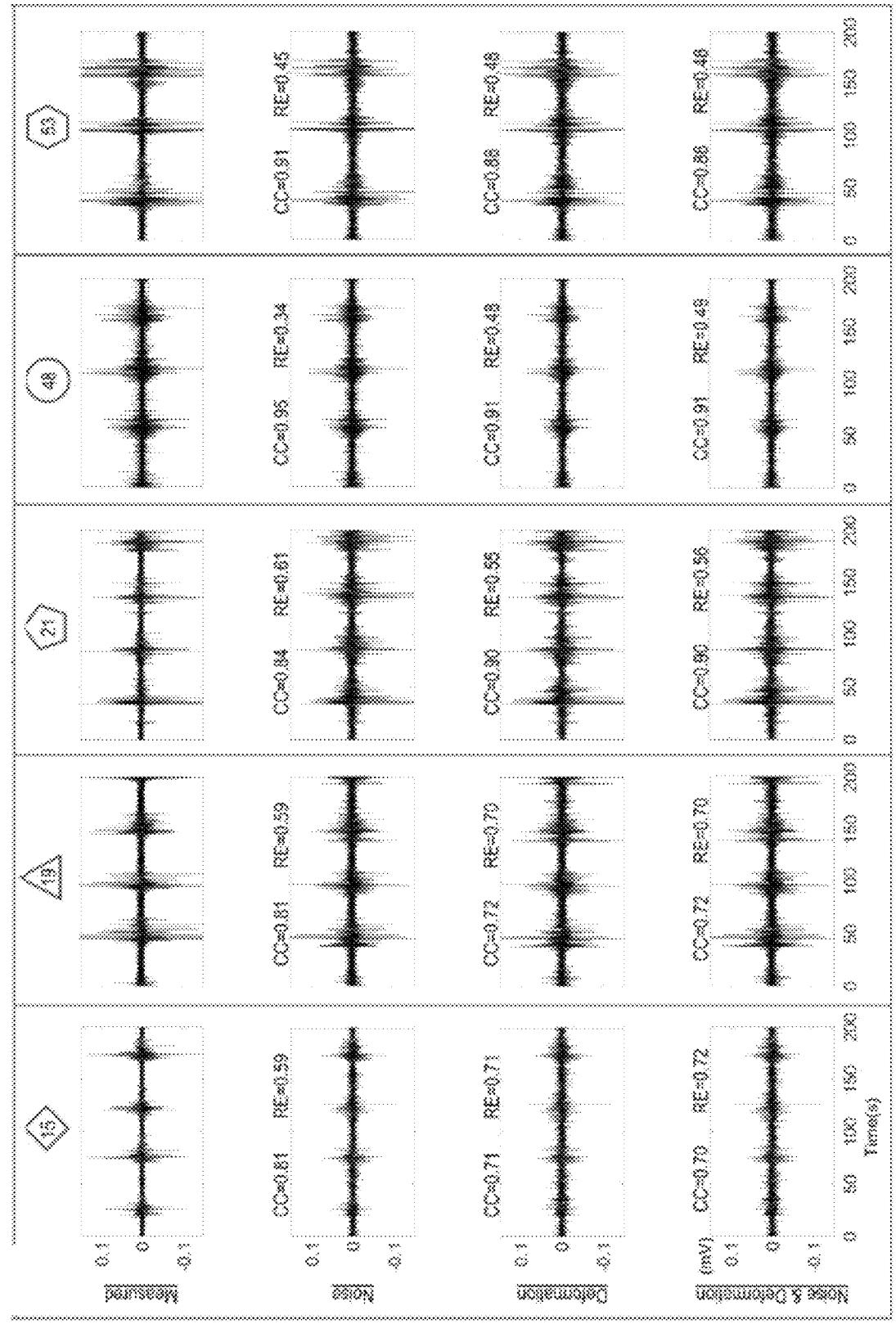
FIG. 4C shows measured and EMMI-reconstructed electrograms (0-200 seconds) from the indicated sites. Analysis of all episodes are presented in Table 1 (N=595)

FIGS. 4A-4C show the data obtained in a study performed to compare EMMI-reconstructed uterine surface electrograms with measured uterine surface electrograms under the indicated conditions in episode #1. FIG. 4A shows a box plot of correlation coefficients (CCs, blue, diamond checkered pattern, defined in Eq. 7) and relative errors (REs, orange, diagonal pattern, Eq. 8) comparing EMMI-reconstructed with measured uterine surface electrograms under the indicated conditions (N=52, see Data file S4). Horizontal lines indicate 1st quartile, median, and 3rd quartile. FIG. 4B shows a left and a right lateral view of sheep uterus, wherein the numbers differentiated by various shapes indicate the discrete uterine surface sites where measured and reconstructed uterine surface electrograms are compared in FIG. 4C. FIG. 4C shows measured and EMMI-reconstructed electrograms (0-200 seconds) from the indicated sites. Analysis of all episodes are presented in Table 1 (N=595).

Figure 8:
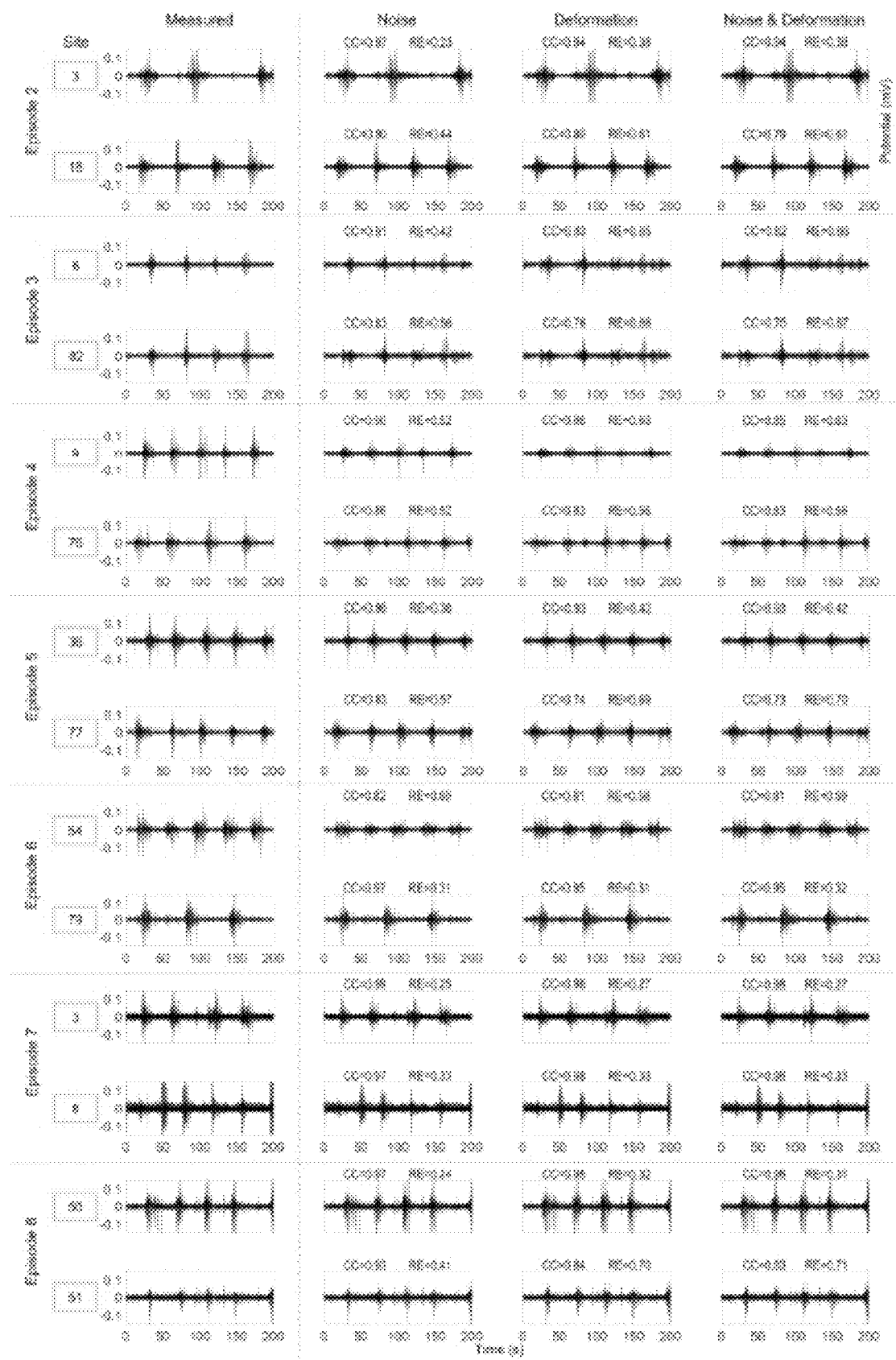
FIG. 8 shows measured electrograms and EMMI-reconstructed uterine surface electrograms in episodes #2-8 of the study of FIGS. 4A-4C.
Figures 9A, 9B, 9C:
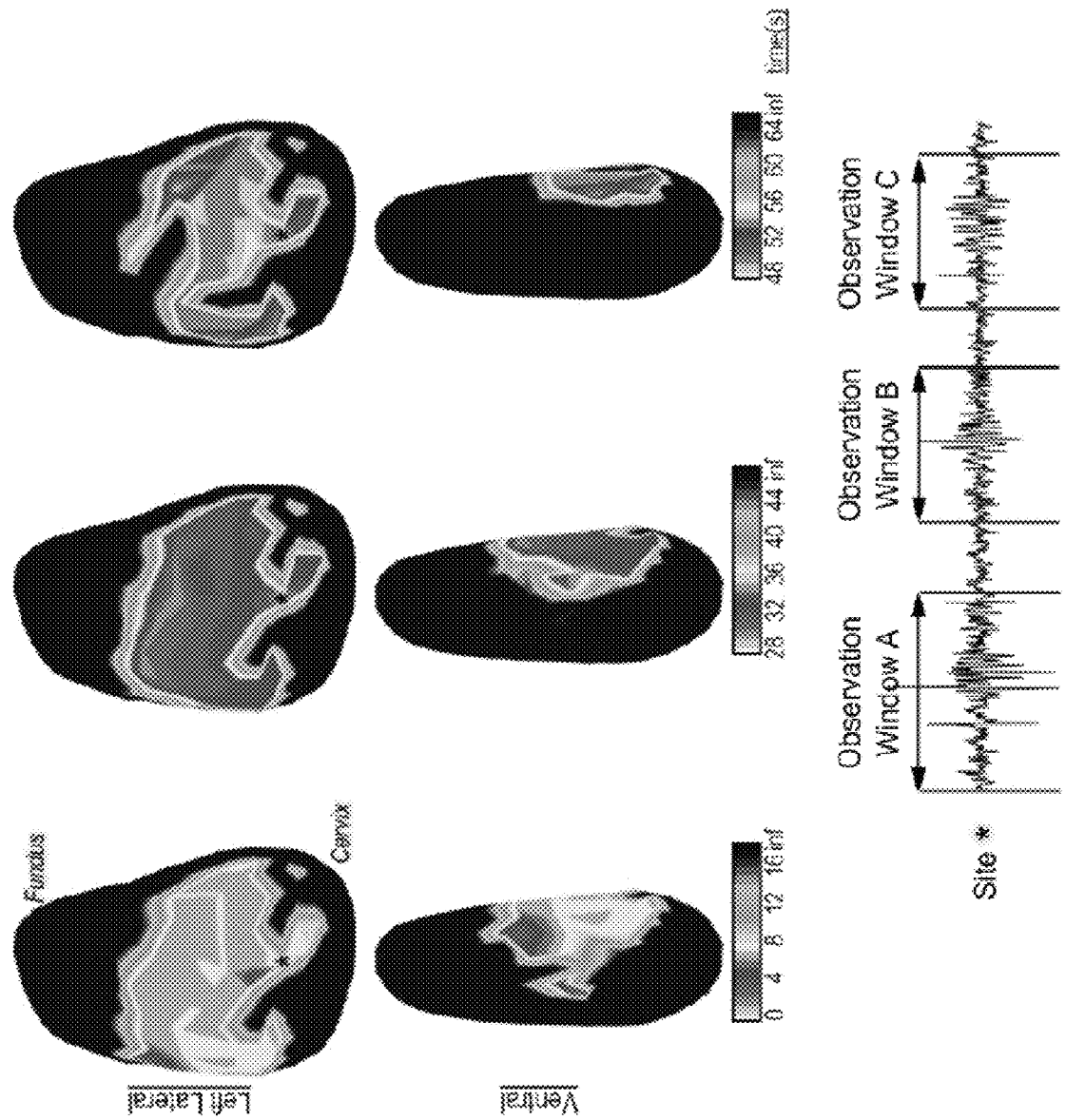
FIG. 9A shows an electrogram and an EMMI-reconstructed activation isochrone map of an oxytocin-induced contraction of the study of FIGS. 7A-7C during observation window A.
FIG. 9B shows an electrogram and an EMMI-reconstructed activation isochrone map of an oxytocin-induced contraction of the study of FIGS. 7A-7C during observation window B.
FIG. 9C shows an electrogram and an EMMI-reconstructed activation isochrone map of an oxytocin-induced contraction of the study of FIGS. 7A-7C during observation window C.
Figures 9D, 9E, 9F:
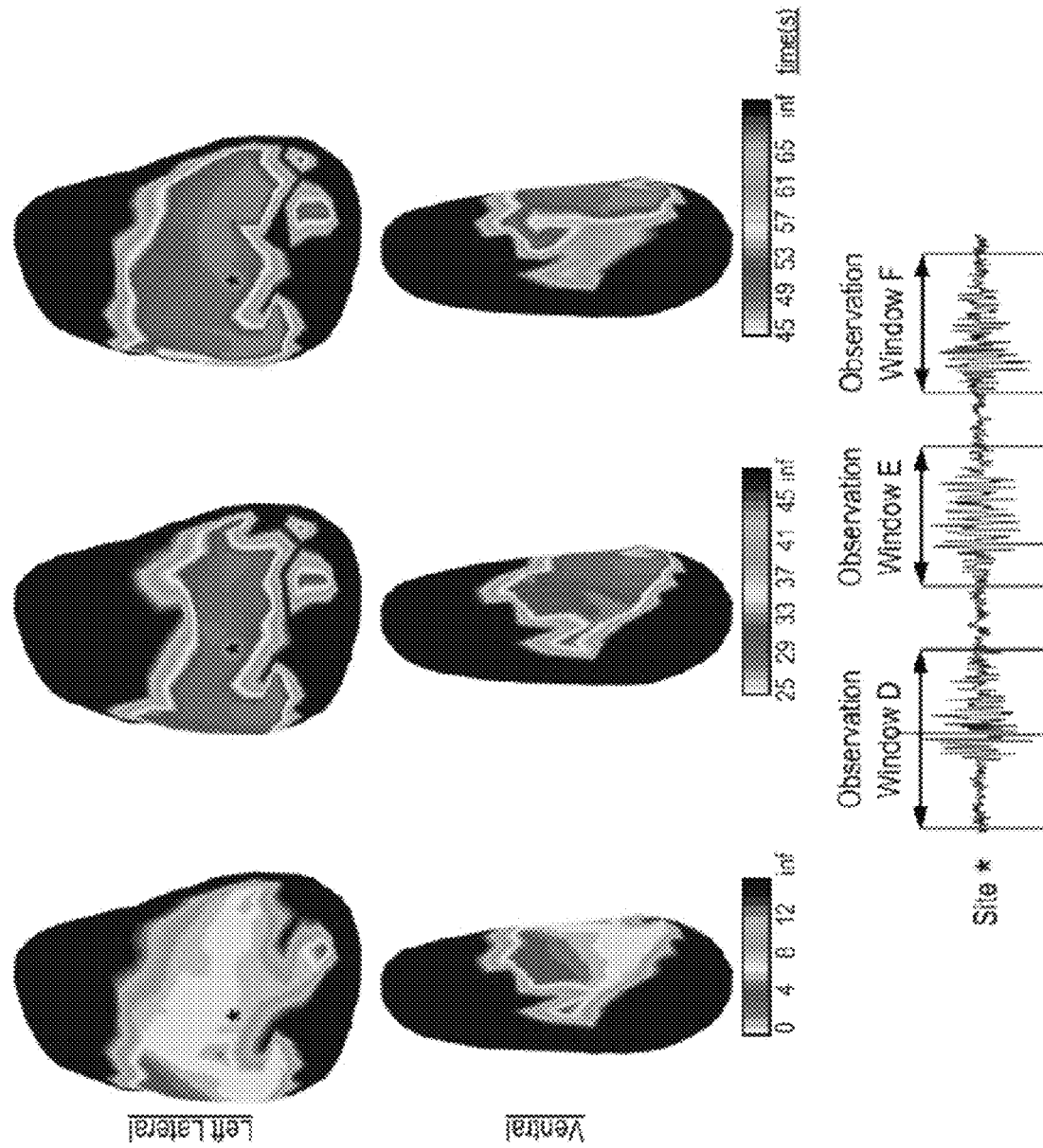
FIG. 9D shows an electrogram and an EMMI-reconstructed activation isochrone map of an oxytocin-induced contraction of the study of FIGS. 7A-7C during observation window D.
FIG. 9E shows an electrogram and an EMMI-reconstructed activation isochrone map of an oxytocin-induced contraction of the study of FIGS. 7A-7C during observation window E.
FIG. 9F shows an electrogram and an EMMI-reconstructed activation isochrone map of an oxytocin-induced contraction of the study of FIGS. 7A-7C during observation window F.

Electrograms were first evaluated in an individual "episode", defined as a recording segment of 300±70 seconds, which typically contained 5-9 electrical bursts at each contracting site. To assess accuracy, CC was calculated, which reflects the correlation between measured and EMMI-reconstructed electrograms over time at each site on the uterine surface, and relative error (RE, see Eq. 8), which reflects the difference in magnitude between measured and EMMI-reconstructed electrograms. Zero RE suggests there is no difference, and high RE suggests a large difference. Therefore, RE has no upper bound. For episode #1, CC and RE were used to compare the measured uterine electrograms at all sites to the corresponding EMMI-reconstructed uterine electrograms to which the following was added: noise, geometrical deformation, or both noise and deformation. In the presence of noise, the median CC was 0.88 [0.73, 0.96] and the median RE was 0.55 [0.32, 0.78]; in the presence of deformation, the median CC was 0.86 [0.71, 0.94] and the median RE was 0.62 [0.41, 0.83]; in the presence of noise and deformation, the median CC was 0.86 [0.70, 0.94] and the median RE was 0.63 [0.41, 0.85] (FIG. 4A). Next, the measured and EMMI-reconstructed uterine electrograms were compared at five representative locations (sites 15, 19, 21, 48, and 53) (FIG. 4B). At these locations, the EMMI-reconstructed electrical burst morphologies were close to the measured electrical burst morphologies (CC from 0.70 to 0.95) under all three conditions (FIG. 4C). The reconstructed electrical amplitudes were also well preserved at all uterine locations (RE from 0.34 to 0.71). The measured and EMMI-reconstructed uterine surface electrograms at two representative locations in episode #2-8 are included in FIG. 8.

The study next evaluated the accuracy of the EMMI-reconstructed electrograms from all eight episodes. Across all eight episodes, CCs were at 0.85 [0.72, 0.95], 0.83 [0.69, 0.93], and 0.83 [0.68, 0.93] under noise, deformation, and noise and deformation respectively; while REs were at 0.55 [0.36, 0.78], 0.62 [0.42, 0.86], and 0.63 [0.43, 0.87] under noise, deformation, and noise and deformation respectively (N=595, see Table 1). Together, these data indicate that EMMI was able to consistently reconstruct accurate uterine electrograms from body surface potential data even in the presence of added noise, geometrical deformation, and both noise and deformation.

TABLE 1

Accuracy analysis of all pacing data, electrograms, potential maps and isochrone maps reconstructed by EMMI

| EMMI Accuracy (Pacing) | N= | Distance Error of Negative Epicenter (mm) Mean ± std | Distance Error of Positive Epicenter (mm) Mean ± std | Angular Error (degree) Mean ± std | Potential Map CC Median [Q1, Q3] |
|---|---|---|---|---|---|
| Sheep A | 138 | 16.5 ± 7.2 | 28.8 ± 11.4 | 6.1 ± 6.5 | 0.71 [0.67, 0.74] |
| Sheep B | 390 | 2.9 ± 0.0 | 8.1 ± 6.3 | 7.5 ± 8.2 | 0.83 [0.81, 0.84] |

| EMMI Robustness | | N= | Median CC [Q1, Q3] | Median RE [Q1, Q3] |
|---|---|---|---|---|
| Electrogram | Noise | 595 | 0.85 [0.72, 0.95] | 0.55 [0.36, 0.78] |
| | Deformation | | 0.83 [0.69, 0.93] | 0.62 [0.42, 0.86] |
| | Noise & Deformation | | 0.83 [0.68, 0.93] | 0.63 [0.43, 0.87] |
| Potential Map | Noise | 28120 | 0.80 [0.71, 0.86] | 0.59 [0.48, 0.73] |
| | Deformation | | 0.78 [0.68, 0.85] | 0.64 [0.52, 0.78] |
| | Noise & Deformation | | 0.77 [0.67, 0.84] | 0.64 [0.53, 0.78] |
| Isochrone Map | Noise | 25 | 0.99 [0.96, 1.00] | 0.01 [0.00, 0.06] |
| | Deformation | | 0.98 [0.95, 0.99] | 0.02 [0.01, 0.08] |
| | Noise & Deformation | | 0.97 [0.94, 1.00] | 0.03 [0.01, 0.08] |

Example 14: EMMI Potential Maps

Figure 5A:
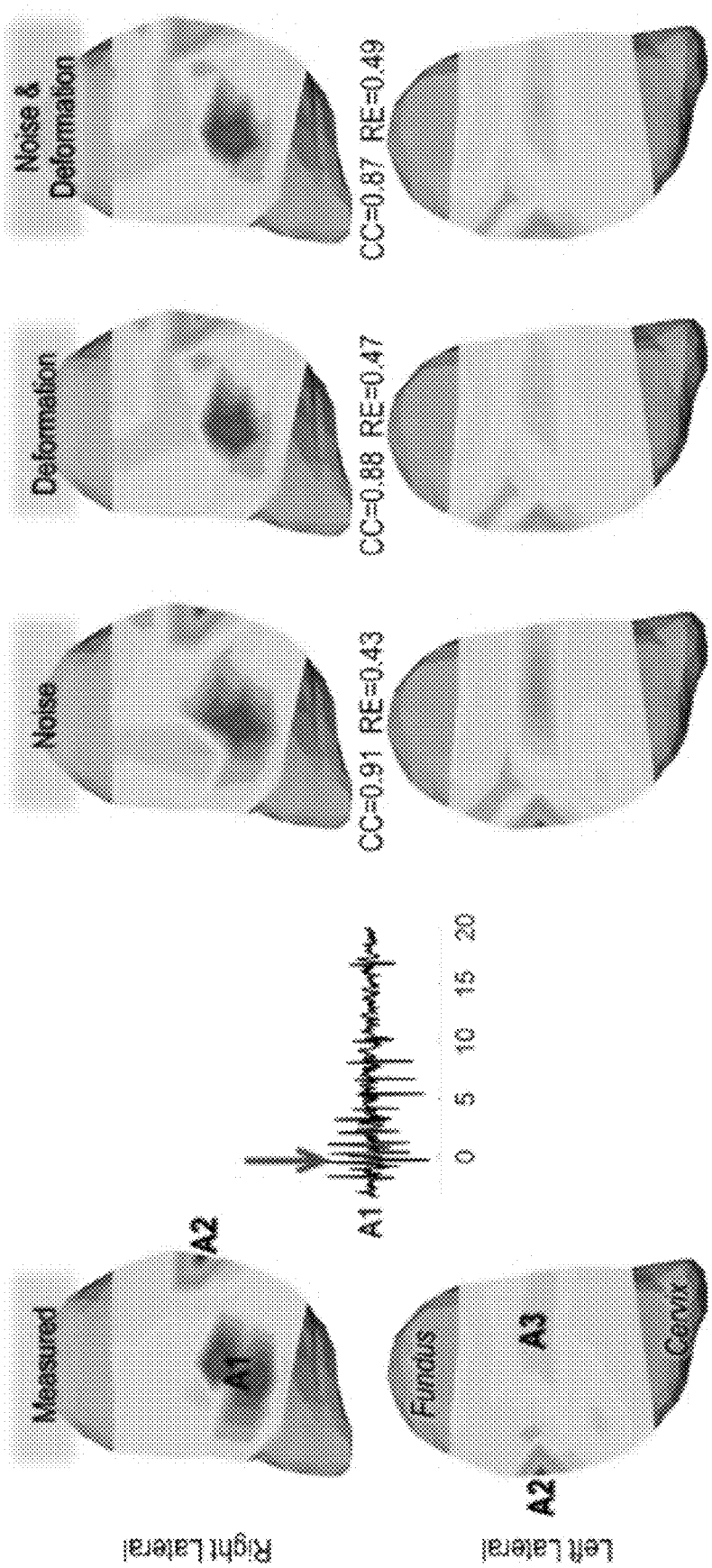
FIG. 5A shows a measured electrogram, measured potential maps, and reconstructed maps with noise, deformation, or both noise and deformation, shown at time instance (red arrows in electrograms) 0 seconds.
Figure 5B:
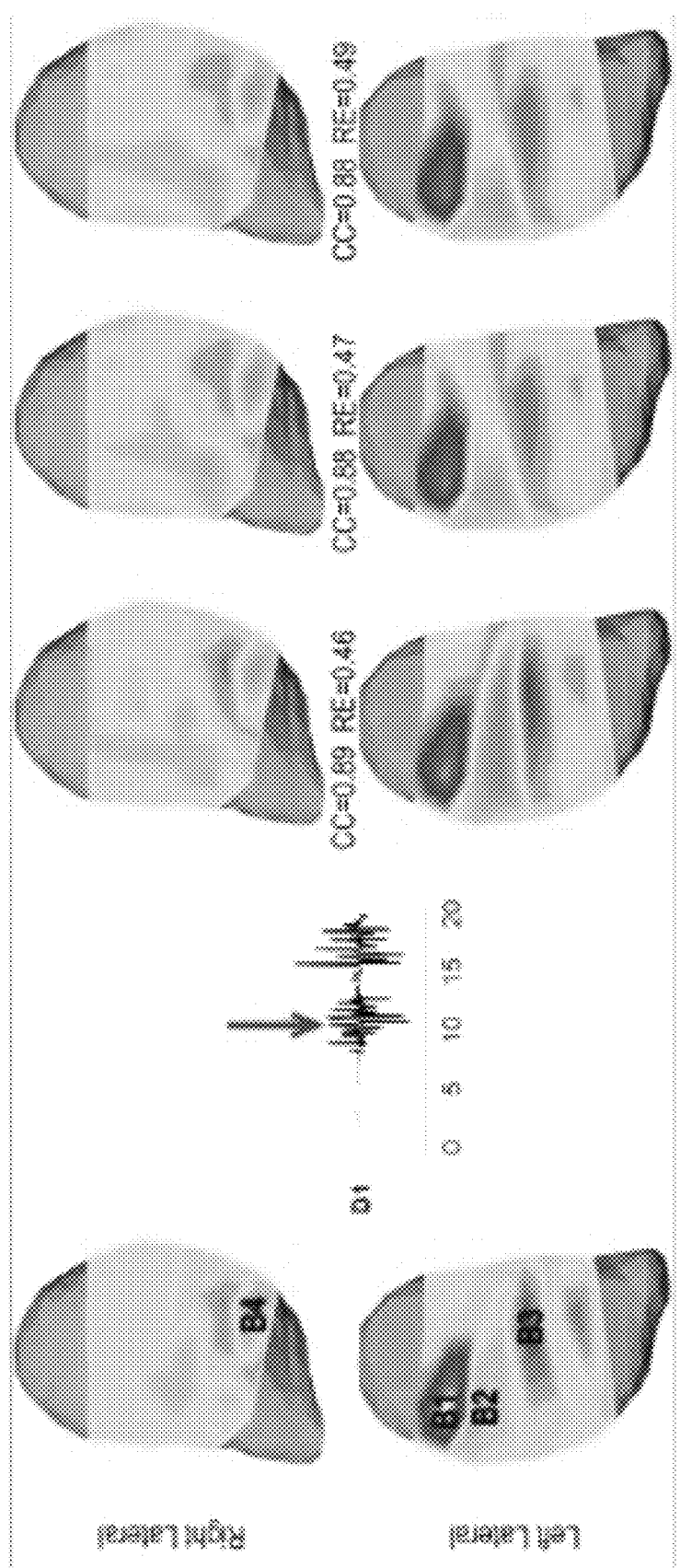
FIG. 5B shows a measured electrogram, measured potential maps, and reconstructed maps with noise, deformation, or both noise and deformation, shown at time instance (red arrows in electrograms) 11 seconds.
Figure 5C:
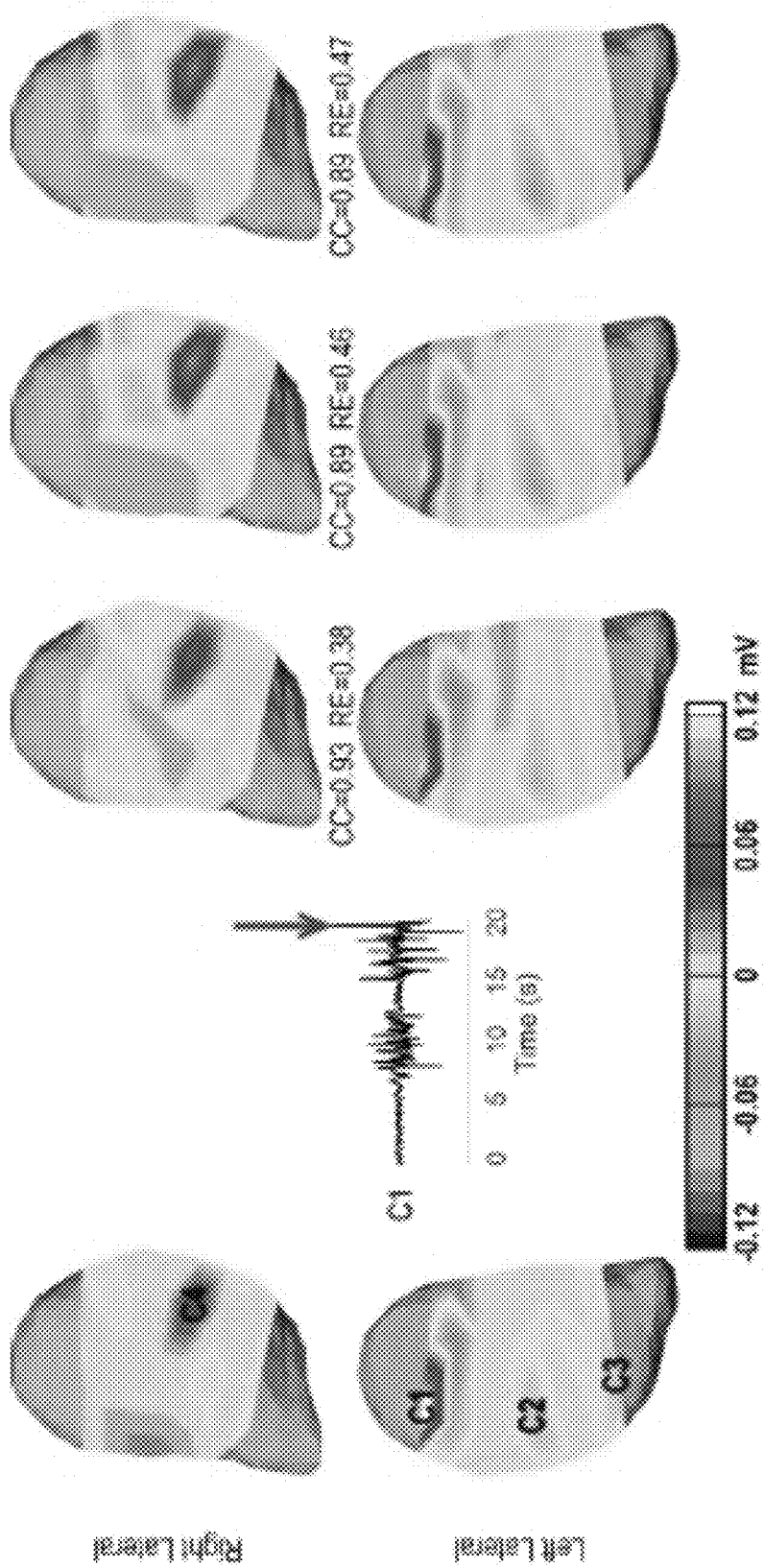
FIG. 5C shows a measured electrogram, measured potential maps, and reconstructed maps with noise, deformation, or both noise and deformation, shown at time instance (red arrows in electrograms) 20 seconds.

The study next compared potential maps measured at the uterine surface to those reconstructed by EMMI in the presence of noise, geometrical deformation, and both noise and deformation. FIGS. 5A-5C show three representative potential maps at different time points (denoted by red arrows in the electrograms) during episode #1:0 seconds (as seen in FIG. 5A), 11 seconds (as seen in FIG. 5B), and 20 seconds (as seen in FIG. 5C). The potential distribution patterns reconstructed by EMMI under noise, geometrical deformation, and both noise and deformation were similar to those directly measured on the uterine surface. In FIG. 5A, the potential distribution patterns labeled A1, A2, and A3 in the measured potential maps were persevered in EMMI-reconstructed potential maps under all three conditions. Quantitatively as labeled in FIGS. 5A-5C, the spatial CC values for the entire potential maps were high (0.87 to 0.93), and the spatial RE values were low (0.38 to 0.49). CC was analyzed (0.80 [0.71, 0.86], 0.78 [0.68, 0.85], and 0.77 [0.67, 0.84]) and RE (0.59 [0.48, 0.73], 0.64 [0.52, 0.78], and 0.64 [0.53, 0.78]) under noise, deformation, and noise and deformation, respectively for 28120 potential maps from eight episodes and summarized in Table 1. The overall similarity between the measured and EMMI-reconstructed potential maps indicate that EMMI can accurately reconstruct uterine surface potential patterns during uterine contraction even in the presence of additional noise, geometrical deformation, and both additional noise and deformation.

Example 15: Isochrone Maps

Figure 6A:
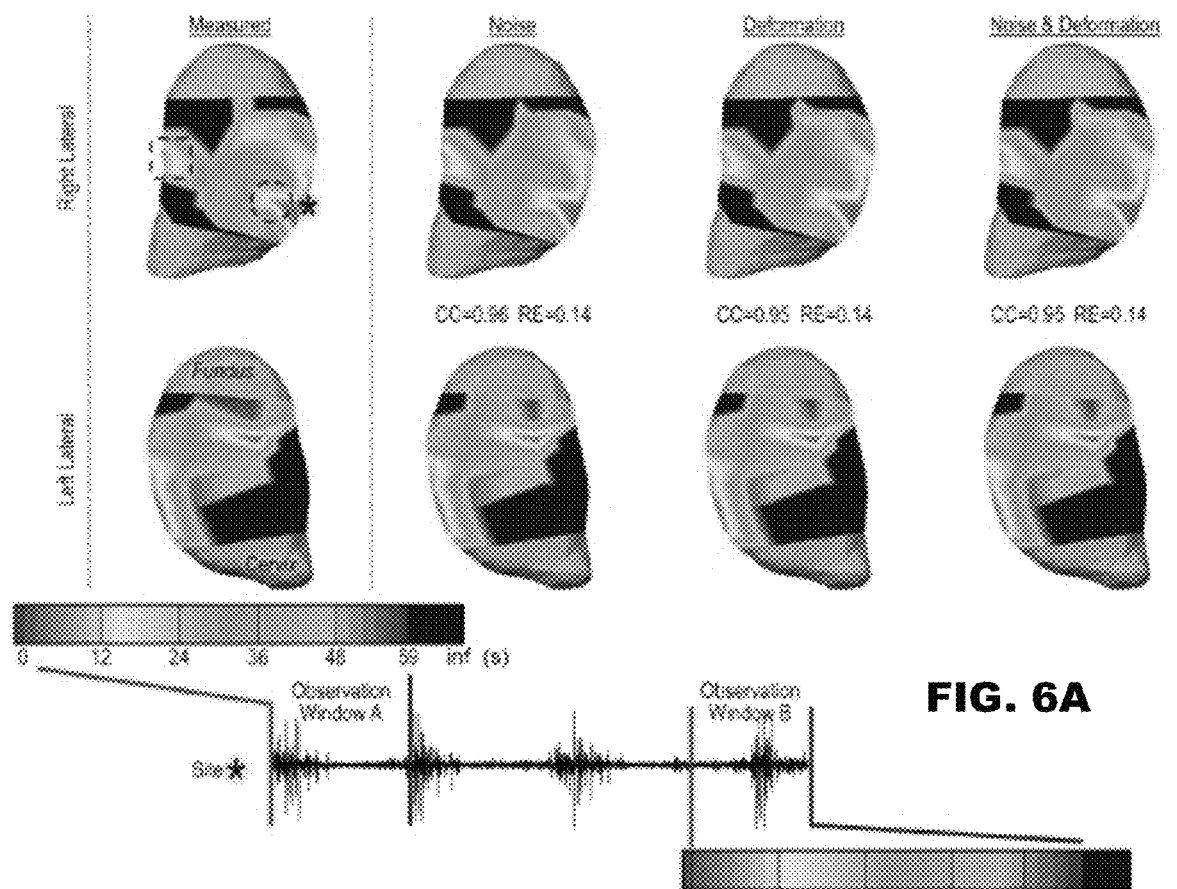
FIG. 6A shows measured and EMMI-reconstructed activation isochrone maps with noise, deformation, or both noise and deformation during observation window A (0-59 seconds)
Figure 6B:
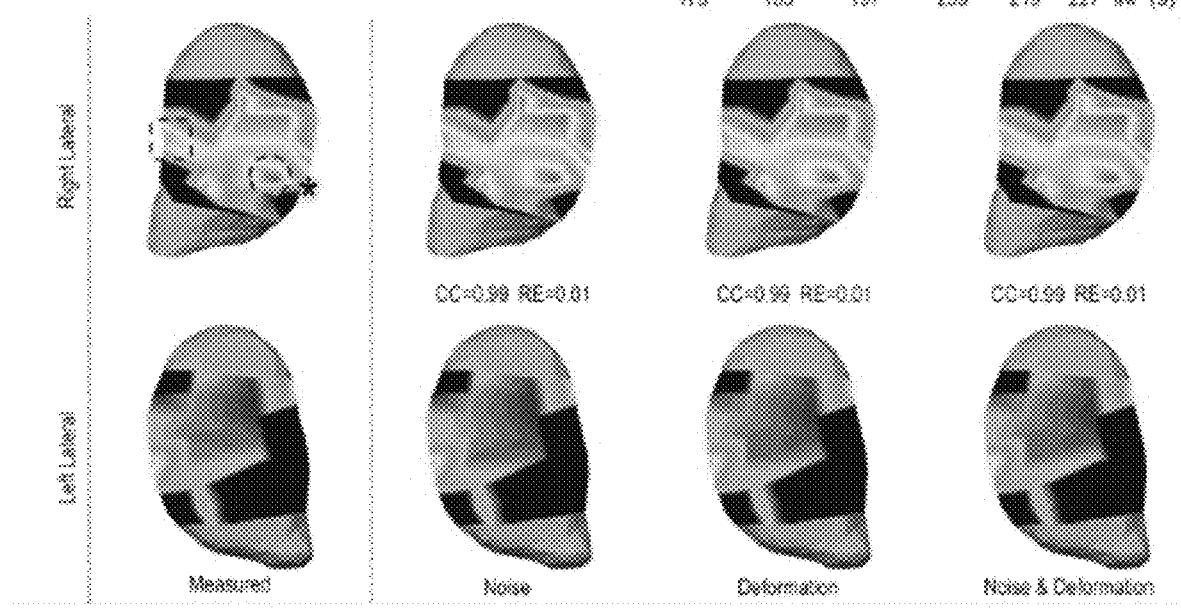
FIG. 6B shows measured and EMMI-reconstructed activation isochrone maps with noise, deformation, or both noise and deformation during observation window B (173-227 seconds)

For assessment of the robustness of EMMI reconstruction, isochrone maps were generated to reflect the electrical activation pattern of the uterus during a particular observation window. Isochrone maps were constructed by using a heat map to denote the activation time of each uterine site; warm colors indicate uterine regions that activated early, and cool colors indicate regions that activated late. FIGS. 6A-6B show isochrone maps for two observation windows, one from 0 to 59 seconds and the other from 173 to 227 seconds in episode #1. The electrogram represents the site marked with an asterisk. In the isochrone maps, red indicates the earliest activation, blue indicates the latest activation, and the darkest blue, labeled 'inf', denotes regions in which no activation was recorded during the observation window. Black dashed circles and squares denote uterine surface areas that activated early in both windows. CCs and REs shown on FIGS. 6A-6B were computed at their corresponding observation windows. In the first observation window (FIG. 6A), early activation was observed (red) in a large region along the fetal spine (maternal ventral) and a small region at left lateral and maternal dorsal, which then locally propagated to nearby regions (yellow and then green in color). In the second observation window (FIG. 6B), early activation in three connected regions at right lateral was observed, which then propagated to left lateral. The uterine sites marked by the black dashed circles and squares activated early in both observation windows. EMMI-reconstructed isochrone maps in the presence of noise, deformation, or both preserved activation patterns in directly measured isochrone maps during both observation windows (observation windows A, CC=0.96, 0.95 and 0.95, RE=0.14, 0.14 and 0.14 under three conditions, respectively; observation windows B, CC=0.99, 0.99 and 0.99, RE=0.01, 0.01 and 0.01 under three conditions, respectively). For all 25 isochrone maps from 8 episodes, CCs are 0.99 [0.96, 1.00], 0.98 [0.95, 0.99], and 0.97 [0.94, 1.00], while REs are 0.01 [0.00, 0.06], 0.02 [0.01, 0.08], and 0.03 [0.01, 0.08] under noise, deformation, and noise and deformation, respectively. These results suggest that EMMI can accurately reconstruct isochrone maps in the presence of noise, deformation, or both.

Example 16: EMMI Feasibility

Finally, the study evaluated the feasibility of EMMI being used to noninvasively map uterine surface potentials from measured body surface potentials. Thus, data collected from the body surface of four sheep was analyzed after at least two oxytocin boluses were delivered before surgery was performed. Body surface electrical activity bursts during uterine contractions were measured and confirmed by two obstetricians (A.G.C, J.S.R.) and one veterinary surgeon (M.T.). The three contiguous uterine contractions were reconstructed by EMMI using the measured body surface potentials and MRI-derived body-uterus geometry. The detailed activation sequences were shown in FIGS. 7A-7C.

Figures 7A, 7B, 7C:
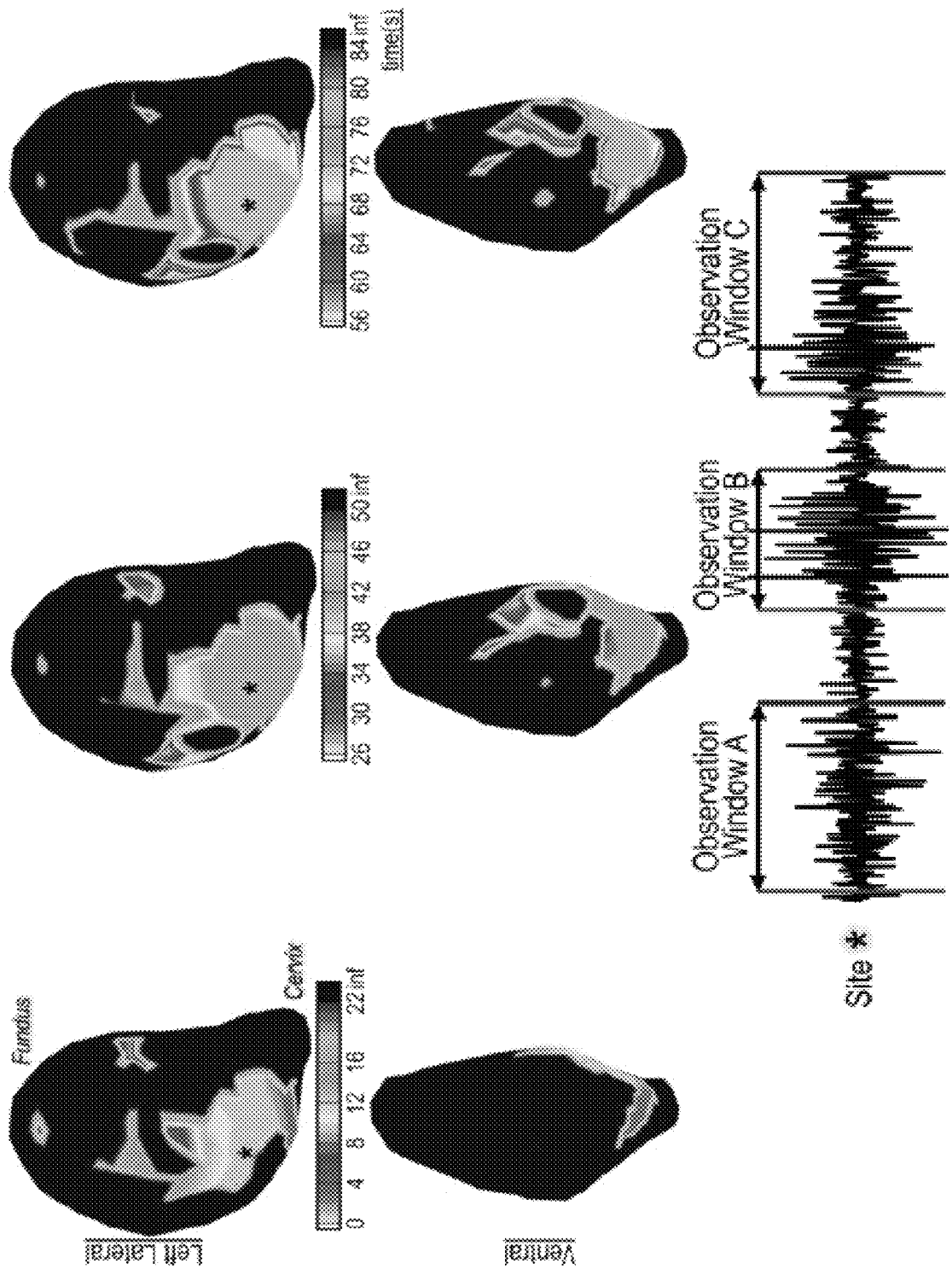
FIG. 7A shows an EMMI reconstructed electrogram and a ventral and left lateral view of EMMI reconstructed activation isochrones maps of oxytocin induced contractions during observation window A.
FIG. 7B shows an EMMI reconstructed electrogram and a ventral and left lateral view of EMMI reconstructed activation isochrones maps of oxytocin induced contractions during observation window B.
FIG. 7C shows an EMMI reconstructed electrogram and a ventral and left lateral view of EMMI reconstructed activation isochrones maps of oxytocin induced contractions during observation window C.

FIGS. 7A-7C show an EMMI reconstructed electrogram of a ventral and a left view of EMMI-reconstructed activation isochrone maps of oxytocin-induced contractions over observation windows A-C, respectively. Three contiguous contractions (0-22 seconds, as seen in FIG. 7A), (26-50 seconds, as seen in FIG. 7B), and (56-84 seconds, as seen in FIG. 7C) mapped by EMMI. The EMMI-reconstructed electrogram is from the uterine surface site denoted by an asterisk. In the isochrone maps, light pink indicates the earliest activation, blue indicates the latest activation, and the darkest blue, labeled 'inf', denotes regions in which no activation was recorded during the observation window.

Other nine uterine contractions were reconstructed by EMMI and the isochrone sequences are shown in FIGS. 9A-9I (Total N=12). The results indicated that EMMI is feasible to image uterine contraction noninvasively.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

What is claimed is:

1. A method for noninvasively reconstructing a plurality of generated three-dimensional images to determine uterine electrical activity of a uterus of a mammal during at least one uterine contraction, the mammal having a body surface surrounding the uterus, the method comprising:

applying a plurality of imaging markers to a plurality of locations on the body surface, each one of the plurality of imaging markers applied to one of the plurality of locations;

performing an imaging scan of the uterus of the mammal, the imaging scan operable to generate a plurality of generated three-dimensional images of the body surface and uterus of the mammal;

determining a body-uterus geometry of the mammal based on the plurality of generated three-dimensional images;

replacing each one of the plurality of imaging markers applied to one of a plurality of locations, with one of a plurality of electrodes, each one of the plurality of electrodes in connection with an electrical recording device and operable to detect body surface electrical potentials of the body surface at each one of the plurality of locations;

recording the body surface electrical potentials via the electrical recording device during the at least one uterine contraction;

generating a plurality of body surface electrical potential maps based on the body-uterus geometry and the plurality of body surface electrical potentials detected at the plurality of locations during the at least one uterine contraction; and reconstructing the plurality of generated three-dimensional images to provide a plurality of reconstructed three-dimensional images representative of the uterine electrical activity of the uterus of the mammal during the at least one uterine contraction from the body-uterus geometry of the mammal and the plurality of body surface electrical potentials, wherein the plurality of reconstructed three-dimensional images comprises a plurality of uterine surface electrical potential maps, wherein the plurality of uterine surface electrical potential maps have a median spatial correlation coefficient of 0.77 or greater when reconstructed in the presence of noise, geometrical deformation, or both noise and deformation as compared to when reconstructed without noise or deformation.

2. The method of claim 1, wherein:
at least a portion of the plurality of imaging markers are visible in at least a portion of the plurality of generated three-dimensional images.

3. The method of claim 1, wherein:
the imaging scan is an MRI scan;
the plurality of generated three-dimensional images include MRI images; and
the plurality of imaging markers includes MRI markers.

4. The method of claim 3, wherein:
the plurality of MRI markers includes up to 256 MRI markers; and
the plurality of electrodes includes up to 256 electrodes.

5. The method of claim 3, wherein:
the number of the plurality of MRI markers is equal to the number of the plurality of electrodes.

6. The method of claim 1, wherein:
the plurality of reconstructed three-dimensional images include a plurality of uterine surface electrical potential maps.

7. The method of claim 1, wherein:
the plurality of reconstructed three-dimensional images include at least one of a plurality of uterine surface electrical potential maps, a plurality of electrograms, or a plurality of isochrones maps generated by assembling local activation time of the body surface electrical potential at each of the plurality of locations during the at least one uterine contraction.

8. A method for noninvasively determining uterine electrophysiology of a uterus of a mammal, the method comprising:
determining a body-uterus geometry of the uterus of the mammal from a plurality of generated three-dimensional images of a body surface and the uterus of the mammal, the body surface surrounding the uterus of the mammal;
detecting a plurality of body surface electrical potentials of the body surface surrounding the uterus of the mammal via a plurality of electrodes, the electrodes in connection with an electrical recording device;
recording the plurality of body surface electrical potentials via the electrical recording device during an observation window; and
determining a uterine surface electrical data by reconstructing the plurality of generated three-dimensional images based on the body-uterus geometry of the mammal and the plurality of body surface electrical potentials,
wherein the plurality of reconstructed three-dimensional images comprises a plurality of uterine surface electrical potential maps, wherein the plurality of uterine surface electrical potential maps have a median spatial correlation coefficient of 0.77 or greater when reconstructed in the presence of noise, geometrical deformation, or both noise and deformation as compared to when reconstructed without noise or deformation.

9. The method of claim 8, wherein determining a body-uterus geometry of the uterus of the mammal includes:
applying a plurality of imaging markers to a plurality of locations on the body surface of the mammal surrounding the uterus;
performing an imaging scan of the uterus of the mammal, the imaging scan operable to generate a plurality of generated three-dimensional images of the body surface and the uterus of the mammal, the plurality of locations visible in the plurality of generated three-dimensional images; and
determining the body-uterus geometry of the mammal based on the plurality of generated three-dimensional images of the mammal and the plurality of locations of the plurality of imaging markers.

10. The method of claim 9, wherein:
each one of the plurality of electrodes replaces one of the plurality of imaging markers, such that each one of the plurality of electrodes is applied to one of the plurality of locations on the body surface of the mammal.

11. The method of claim 9, wherein:
the plurality of generated three-dimensional images include MRI images; and
the plurality of imaging markers includes MRI markers.

12. The method of claim 11, wherein:
the number of the plurality of MRI markers is equal to the number of the electrodes.

13. The method of claim 8, wherein:
the uterine surface electrical data includes a plurality of reconstructed three-dimensional images representative of the electrical activity of the uterus during at least one uterine contraction.

14. The method of claim 13, wherein:
the plurality of reconstructed three-dimensional images representative of the electrical activity of the uterus during at least one uterine contraction include at least one selected from the group of uterine surface electrical potential maps, electrograms, or isochrones maps.

15. The method of claim 14, wherein:
the electrograms and isochrones maps are derived from the uterine surface electrical potential maps.

16. A system for noninvasively determining uterine surface electrical activity of a mammal during at least one uterine contraction, the system comprising:
a plurality of imaging markers, each one of the plurality of imaging markers operable to be secured to one of a plurality of locations on a body surface surrounding a uterus of a mammal;
an imaging modality that is substantially safe for use during pregnancy and is operable to provide a plurality of generated three-dimensional images of the body surface and the uterus of the mammal, the plurality of imaging markers visible on the plurality of generated three-dimensional images;
a plurality of electrodes, each one of the plurality of electrodes operable to replace one of the plurality of imaging markers and detect a plurality of electrical signals on the body surface surrounding the uterus of the mammal during the at least one uterine contraction;
an electrical mapping device connected to the electrodes and operable to record the plurality of electrical signals detected at each of the plurality of electrodes during the at least one uterine contraction; and
at least one non-transitory computer readable medium storing instructions which when executed by at least one processor, cause the at least one processor to:

receive the plurality of generated three-dimensional images from the imaging modality;
determine the plurality of locations based on the imaging markers visible in the plurality of generated three-dimensional images;
determine a body-uterus geometry of the mammal based on the plurality of three-dimensional images and the plurality of locations;
receive the plurality of electrical signals from the electrical mapping device; and
generate a plurality of body surface electrical potential maps based on the body-uterus geometry and the plurality of electrical signals; and
generate a plurality of three-dimensional uterine surface electrical potential maps based on the body-uterus geometry and the plurality of body surface electrical potential maps,
wherein the plurality of uterine surface electrical potential maps have a median spatial correlation coefficient of 0.77 or greater when generated in the presence of noise, geometrical deformation, or both noise and deformation as compared to when generated without noise or deformation.

17. The system of claim 16, wherein:
the processor is further operable to derive electrograms and isochrones maps from the uterine surface electrical potential maps.

18. The system of claim 16, further comprising a display operable to display the plurality of three-dimensional uterine surface electrical potential maps.

19. The system of claim 16, wherein:
the body surface electrical potential maps represent a distribution of the electrical signals determined during the uterine contraction; and
the uterus surface electrical potential maps represent a distribution of the electrical signals detected during the uterine contraction.

* * * * *